(12) United States Patent
Abbott et al.

(10) Patent No.: US 8,143,254 B2
(45) Date of Patent: Mar. 27, 2012

(54) METHODS FOR MODULATING ION CHANNELS

(75) Inventors: Geoffrey W. Abbott, Crompond, NY (US); Robert Engel, Carle Place, NY (US); JaimeLee Iolani Rizzo, Glen Cove, NY (US)

(73) Assignees: Cornell Research Foundation, Inc., Ithaca, NY (US); Pace University, New York, NY (US); Research Foundation of City University of New York, New York, NY (US)

( * ) Notice: Subject to any disclaimer, the term of this patent is extended or adjusted under 35 U.S.C. 154(b) by 263 days.

(21) Appl. No.: 11/884,628

(22) PCT Filed: Feb. 17, 2006

(86) PCT No.: PCT/US2006/005750
§ 371 (c)(1),
(2), (4) Date: Jun. 3, 2008

(87) PCT Pub. No.: WO2006/089168
PCT Pub. Date: Aug. 24, 2006

(65) Prior Publication Data
US 2009/0005386 A1 Jan. 1, 2009

Related U.S. Application Data

(60) Provisional application No. 60/654,531, filed on Feb. 18, 2005.

(51) Int. Cl.
*A01N 43/58* (2006.01)

(52) U.S. Cl. ........................ 514/249

(58) Field of Classification Search .................. 544/382; 548/335.1
See application file for complete search history.

(56) References Cited

U.S. PATENT DOCUMENTS

| | | |
|---|---|---|
| 3,198,705 A | 8/1965 | Cummings et al. |
| 3,577,540 A | 5/1971 | Myers et al. |
| 4,060,652 A | 11/1977 | Khromov-Borisov et al. |
| 4,259,354 A | 3/1981 | Molloy et al. |
| 4,352,820 A | 10/1982 | Scurlock et al. |
| 4,400,397 A | 8/1983 | Arias Alvarez et al. |
| 4,402,982 A | 9/1983 | Alvarez et al. |
| 4,661,509 A | 4/1987 | Gordon et al. |

(Continued)

FOREIGN PATENT DOCUMENTS

WO WO00/01676 1/2000

(Continued)

OTHER PUBLICATIONS

Wei et al (Potassium Channel Blockers attenuate hypoxia- and ischemia-induced neural death in vitro and en vivo).*

(Continued)

*Primary Examiner* — Brandon Fetterolf
*Assistant Examiner* — Jean Cornet
(74) *Attorney, Agent, or Firm* — Hoffmann & Baron, LLP

(57) ABSTRACT

In one embodiment, the invention provides an ion having the formula: (I) In another embodiment, the invention provides a method for modulating potassium, sodium, and cyclic nucleotide-modulated ion channels in a mammal in need thereof. In a further embodiment, the invention provides a method for modulating ligand-gated ion channels or transient receptor potential channels in a mammal in need thereof. The methods comprise administering an ion having the formula described above.

20 Claims, 5 Drawing Sheets

U.S. PATENT DOCUMENTS

| | | | |
|---|---|---|---|
| 4,820,737 | A | 4/1989 | Schoenwald et al. |
| 4,898,888 | A | 2/1990 | Baldone |
| 4,935,448 | A | 6/1990 | Baldone |
| 5,331,014 | A | 7/1994 | Kimura et al. |
| 5,459,126 | A | 10/1995 | Langer et al. |
| 5,627,171 | A | 5/1997 | Park et al. |
| 5,686,448 | A | 11/1997 | Baldone |
| 5,866,562 | A | 2/1999 | Schohe-Loop et al. |
| 5,958,397 | A | 9/1999 | Smerbeck et al. |
| 6,025,399 | A | 2/2000 | Travers et al. |
| 6,110,972 | A | 8/2000 | Fabiano et al. |
| 6,121,289 | A | 9/2000 | Houdi |
| 6,399,663 | B1 | 6/2002 | Haces et al. |
| 6,531,512 | B1 | 3/2003 | Kramer et al. |
| 6,689,814 | B1 | 2/2004 | Argy et al. |

FOREIGN PATENT DOCUMENTS

| | | |
|---|---|---|
| WO | WO01/02406 | 1/2001 |

OTHER PUBLICATIONS

Wempe "Quaternary ammonium ions can externally block voltage-gated K+ channel. Establishing a theoretical and experimental model that predicts KDS and the selectivity of K+ over Na+ ions", Journal of Molecular Structure vol. 562, (2001), pp. 63-78.*

Galanakis et al "Synthesis and Structure-Activity relationships of Dequalinium analogues as K+ channel blockers. Investigations on the role of the charged heterocycle", J. Med. Chem. 1995, vol. 38, pp. 3536-3546.*

Huang et al "Potassium channel blocker TEA prevents CA1 hippocampal injury following forebrain ischemia in adult rats", Neuroscience letters, vol. 305, (2001) pp. 83-86.*

Nakashima et al. (In vivo electrophysiological effects of a selective slow delayed-rectifier potassium channel blocker in anesthetized dogs: potential insights into class III actions, Cardiovascular research 61, (2004) 705-714).*

Wei et al (Potassium Channel Blockers attenuate hypoxia- and ischemia-induced neural death in vitro and en vivo), Stroke. 2003;34:1281-1286.*

Dunn et al., "Discrimination between subtypes of apamin-sensitive Ca2+ – activated K+ channels by gallamine and a novel bis-quaternary quinolinium cyclophane, UCL 1530", British Journal of Pharmacology (1996) 117, pp. 35-42, 1996 Stockton Press.

Clapham, David E., "TRP channels as cellular sensors", Nature, vol. 426, pp. 517-524, Dec. 4, 2003, 2003 Nature Publishing Group.

Coghlan, et al., "Recent Developments in the Biology and Medicinal Chemistry of Potassium Channel Modulators: Update from a Decade of Progress", 2001 American Chemical Society, vol. 44, No. 11, pp. 1627-1653. May 24, 2001.

Chen, et al., "Bis-Quinolinium Cyclophanes: 8,14-Diaza-1,7 (1,4)-diquinolinacyclo-tetradecaphane (UCL 1848), a Highly Potent and Selective, Nonpeptidic Blocker of the Apamin-Sensitive Ca2+– Activated K+ Channel", J. Med. Chem. 2000, pp. 3478-3481, 2000 American Chemical Society.

Rosa, et al., "Bis-Quinolinium Cyclophanes: 6,10-Diaza-3 (1,3),8(1,4)-dibenza-1,5 (1,4)-diquinolinacyclodecaphane (UCL 1684), the First Nanomolar, Non-Peptidic Blocker of the Apamin-Sensitive Ca2+– Activated K+ Channel", J. Med. Chem. 1998, 41, pp. 2-5, 1988 American Chemical Society.

Rosa et al., "Bis-Quinolinium Cyclophanes: A Novel Class of Potent Blockers of the Apamin-Sensitive Ca2+– Activated K+ Channel", Bioorganic & Medicinal Chemistry Letters, vol. 7, No. 1, pp. 7-10, 1997, 1996 Elsevier Science Ltd.

Ludwig, et al., "Structure and Function of Cardiac Pacemaker Channels", Cellular Physiology and Biochemistry, 1999, 9:179-186, 1999 S. Karger AG, Basel.

Catterall, et al., "International Union of Pharmacology. XXXIX. Compendium of Voltage-Gated Ion Channels: Sodium Channels", Pharmacological Reviews, 2003, American Society for Pharmacology and Experimental Therapeutics, vol. 55, No. 4, pp. 575-578.

Catterall, W.A., "Molecular mechanisms of gating and drug block of sodium channels." Sodium Channels and Neuronal Hyperexcitability—No. 241, Novartis Foundation, Wiley Publisher, Jan. 2002, pp. 206-225.

Imoto, K. "Chapter 1 Structure and Functions of Voltage-Dependent Na+ Channels." Pharmacology of Ionic Channel Function: Activators and Inhibitors (Handbook of Experimental Pharmacology) (vol. 147), Springer Publisher; 1 edition (Sep. 6, 2000), pp. 3-26.

Grant, A.O., "Chapter 2 Sodium Channel Blockers and Activators." Pharmacology of Ionic Channel Function: Activators and Inhibitors (Handbook of Experimental Pharmacology) (vol. 147), Springer Publisher; 1 edition (Sep. 6, 2000), pp. 27-51.

Pongs, O, et al., "Chapter 7 Pharmacology of Voltage-Gated Potassium Channels." Pharmacology of Ionic Channel Function: Activators and Inhibitors (Handbook of Experimental Pharmacology) (vol. 147), Springer Publisher; 1 edition (Sep. 6, 2000), pp. 177-196.

Latorre, R, et al., "Chapter 8 Voltage-gated calcium modulated potassium channel of large unitary conductance: structure, diversity and pharmacology." Pharmacology of Ionic Channel Function: Activators and Inhibitors (Handbook of Experimental Pharmacology) (vol. 147), Springer Publisher; 1 edition (Sep. 6, 2000), pp. 197-223.

Nichols, C.G. "Chapter 9 Classical Inward Rectifying Potassium Channels: Mechanisms of Inward Rectification." Pharmacology of Ionic Channel Function: Activators and Inhibitors (Handbook of Experimental Pharmacology) (vol. 147), Springer Publisher; 1 edition (Sep. 6, 2000), pp. 225-242.

Drici, M.-D et al., "Chapter 14 Cardiac K+ Channels and Inherited Long QT Syndrome." Pharmacology of Ionic Channel Function: Activators and Inhibitors (Handbook of Experimental Pharmacology) (vol. 147), Springer Publisher; 1 edition (Sep. 6, 2000), pp. 347-362.

Grunwald, M.E. et al., "Chapter 22 Cyclic Nucleotide-Gated Channels: Classification, Structure and Function, Activators and Inhibitors." Pharmacology of Ionic Channel Function: Activators and Inhibitors (Handbook of Experimental Pharmacology) (vol. 147), Springer Publisher; 1 edition (Sep. 6, 2000), pp. 561-579.

Catterall, Wa et al., (eds.), "Cyclic nucleotide-modulated channels." The International Union of Pharmacology Compendium of Voltage-Gated Ion Channels. (2002) pp. 193-196.

Hansen, et al., "Inhibition of Insulin Secret as a New Drug Target in the Treatment of Metabolic Disorders", Current Medicinal Chemistry, 2004, 11, pp. 1595-1615, 2004 Bentham Science Publishers Ltd.

Vergara, et al., "Calcium-activated potassium channels", Current Opinion in Neurobiology 1998, 8:321-329.

Rosa, et al., "Synthesis, Molecular Modeling, and Pharmacological Testing of Bis-Quinolinium Cyclophanes: Potent, Non-Peptidic Blockers of the Apamin-Sensitive Ca2+– Activated K+ Channel", J. Med. Chem. 2000, 43, 420-431, 2000 American Chemical Society.

Rosenbaum, et al., "Dequalinium: A Novel, High-Affinity Blocker of CNGA1 Channels", J. Gen. Physiol., The Rockefeller University Press, vol. 121, Jan. 2003, pp. 37-47.

Castle, et al., "Dequalinium: a potent inhibitor of apamin-sensitive K+ channels in hepatocytes and of nicotinic responses in skeletal muscle", European Journal of Pharmacology, 236, (1993), pp. 201-207, 1993 Elsevier Science Publishers B.V.

Viswanathan, et al., "Inherited Sodium Channelopathies a Continuum of Channel Dysfunction", TCM vol. 14, No. 1, pp. 28-35, 2004 Elsevier Inc.

Balser, Jeffrey R., "Basic Cardiac Electrophysiology; The Cardiac Sodium Channel: Gating Function and Molecular Pharmacology", J. Mol. Cell. Cardiol. 33, 599-613 (2001), 2001 Academic Press.

Hemmings, Hugh C. Jr., "Neuroprotection by Na+ Channel Blockade", J. Neurosurg Anesthesiol, vol. 16, No. 1, Jan. 2004, Lippincott Williams & Wilkins (2003).

Lai, et al., "The role of voltage-gated sodium channels in neuropathic pain", Current Opinion in Neurobiology 2003, 13:291-297, 2003 Elsevier Science Ltd.

Rogawski, et al., "The neurobiology of antiepileptic drugs for the treatment of nonepileptic conditions", Nature Medicine, vol. 10, No. 7, Jul. 2004, pp. 685-692.

Anantharam, et al., "Pharmacogenetic Considerations in Diseases of Cardiac Ion Channels", The Journal of Pharmacology and Experimental Therapeutics, vol. 37, No. 3, pp. 831-838, 2003 American Society for Pharmacology and Experimental Therapeutics.

Sikes, et al., "Therapeutic Approaches Targeting Prostate Cancer Progression Using Novel Voltage-Gated Ion Channel Blockers", Clinical Prostate Cancer, vol. 2, No. 3, 181-187, 2003.

Lai, et al., "Voltage-Gated Sodium Channels and Hyperalgesia", Annu. Rev. Pharmacol. Toxicol. 2004, 44:371-397, 2004 Annual Reviews.

Wickenden, Alan D., "K+ channels as therapeutic drug targets", Pharmacology & Therapeutics 94 (2002), pp. 157-182, 2002 Elsevier Science Inc.

Shah, et al., "The pharmacology of hSK1 Ca2+ -activated K+ channels expressed in mammalian cell lines", British Journal of Pharmacology (2000) 129, pp. 627-630, 2000 Macmillan Publishers Ltd.

Cooper, et al., "M-Channels; Neurological Diseases, Neuromodulation, and Drug Development", Arch Neurol, vol. 60, Apr. 2003, 2003 American Medical Association.

Endo M, "Preface" (2000) in Handbook of Experimental Pharmacology, Pharmacology of Ionic Channel Function: Activators and Inhibitors, eds Endo M, Kurachi Y, Mishina M (Springer, Heidelberg), 147, preface.

Catterall, WA et al., (eds.), "Voltage-Gated Sodium Channels." The International Union of Pharmacology Compendium of Voltage-Gated Ion Channels. (2002) pp. 11-189.

* cited by examiner (C$_{16}$) TA279 ortho (JSG17)   meta (TA37)   para (JC.638.2a)

■ 250 μM TG28
☐ washout

■ control
☐ JC279.3a (opener)
○ JC638.2a (blocker)

METHODS FOR MODULATING ION CHANNELS

This application asserts priority to U.S. Provisional Application Ser. No. 60/654,531 filed on Feb. 18, 2005, the specification of which is hereby incorporated by reference in its entirety.

BACKGROUND OF THE INVENTION

Ion channels are transmembrane proteins which generally catalyze the transport of ions across cell membranes. The ion channels participate in processes as diverse as the generation and timing of action potentials, synaptic transmissions, secretion of hormones, contraction of muscles, etc.

The family of cation channels typically mediates electrical activity. This family includes potassium, sodium and cyclic nucleotide-modulated ion channels. It is reported that these ion channels play an important role in many physiological processes, including the regulation of heart rate, muscle contraction, neurotransmitter release, neuronal excitability, cell proliferation, etc. Thus, aberrations in the activity of these channels are responsible for many diseases and conditions.

Accordingly, it would be beneficial to modulate ion channels in diseases and conditions characterized by aberrant activity in potassium, sodium and cyclic nucleotide-modulated ion channels. Thus, there is a need for a method for modulating potassium, sodium and cyclic nucleotide-modulated ion channels in mammals suffering from such diseases and conditions.

SUMMARY OF THE INVENTION

The above objectives have been met by the present invention which provides, in one embodiment, an ion comprising the following formula:

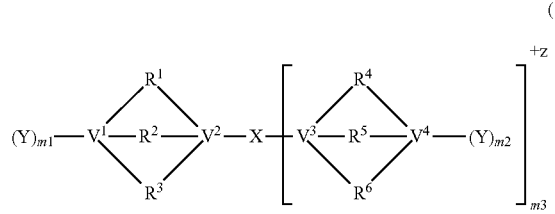

(1)

wherein:

each of $R^1$, $R^2$, $R^3$, $R^4$, $R^5$, $R^6$, independently of each other, represents an acyclic hydrocarbon group having one to four carbon atoms;

each of X and Y independently represents a carbocyclic or heterocyclic, saturated or unsaturated, substituted or unsubstituted ring or fused ring system; an acyclic hydrocarbon group having one to twenty six carbons atoms; or a combination thereof;

m1, m2, and m3 independently represent 0 or 1;

$V^1$ and $V^4$ independently represent C, N, or $N^+$;

$V^2$ and $V^3$ independently represent C or $N^+$;

z represents the number of positive charges in the ion and has a value of at least 1;

wherein any of said acyclic hydrocarbon groups is saturated or unsaturated, substituted or unsubstituted, straight-chained or branched, and wherein one or more carbon atoms of the acyclic hydrocarbon group is optionally substituted by one or more heteroatoms, wherein no heteroatom is bound to: another heteroatom, $V^1$ when $V^1$ is N or $N^+$,
$V^2$ when $V^2$ is $N^+$,
$V^3$ when $V^3$ is $N^+$, or
$V^4$ when $V^4$ is N or $N^+$; and provided that at least one of $V^1$, $V^2$, $V^3$, and $V^4$ represents $N^+$.

In another embodiment, the invention provides a method for modulating potassium, sodium, and cyclic nucleotide-modulated ion channels in a mammal in need thereof. The method comprises administering to the mammal an effective amount of an ion as described above.

In yet another embodiment, the invention provides a method for modulating ligand-gated ion channels or transient receptor potential channels in a mammal in need thereof. The method comprises administering to the mammal an effective amount of an ion as described above.

DETAILED DESCRIPTION OF THE INVENTION

Figure 1A:
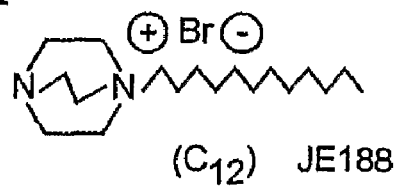
FIG. 1. MiRP2 alters Kv2.1 block by JE 188. (A) The structure of compound JE 188. (B) Representative traces of current recorded in *Xenopus* oocytes using TEVC, and voltage protocol in upper left. Oocytes were injected with cRNA encoding Kv2.1+/−cRNA encoding MiRP2, as indicated. Scale as indicated in lower left. 'Control' trace (solid line) was recorded after 5 pulses in 4 mM KCl bath medium (pH 7.4) in the absence of drug. Dashed line indicates a trace during pulsing in the presence of 250 μM JE188. (C) Mean current inhibition assessed by comparison of peak current at various drug concentrations with peak current before drug application (n=5-6 oocytes per point; error bars indicate SEM). Drug block was reversible upon washout, and traces that did not recover to control peak current (+/−10%) upon washout were discarded.

The invention is based on the surprising discovery by the inventors that certain positively charged ions modulate potassium, sodium, and cyclic nucleotide-modulated ion channels.

Ions

In one aspect, the present invention relates to a positively charged ion comprising the following formula:

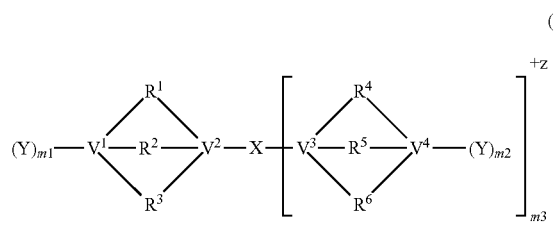

(1)

In formula (1), V$^1$ and V$^4$ independently represent C, N, or N$^+$; and V$^2$ and V$^3$ independently represent C or N$^+$. At least one of V$^1$, V$^2$, V$^3$, and V$^4$ represents N$^+$.

The symbol z represents the total number of positive charges in the ion. Positive charge z results from positively charged nitrogen atoms (N$^+$) in the ion. The positively charged nitrogen atoms in the ion include those as provided in V$^1$, V$^2$, V$^3$, and V$^4$.

At least one of V$^1$, V$^2$, V$^3$, and V4 in the ion represent N$^+$. Accordingly, z is required to represent at least 1. For example, when m3 is 1, then at least one of V$^1$, V$^2$, V$^3$, and V4 represent N$^+$, Similarly, when m3 is 0, then at least one of V$^1$ and V$^2$ represent N$^+$.

R$^1$, R$^2$, R$^3$, R$^4$, R$^5$, R$^6$, X and Y may independently represent an acyclic hydrocarbon group.

The acyclic hydrocarbon group contains a minimum of one carbon atom. Preferably, the acyclic hydrocarbon group independently in each of R$^1$, R$^2$, R$^3$, R$^4$, R$^5$, R$^6$, X and Y contains a minimum of two carbon atoms. Preferably, the acyclic hydrocarbon group in X contains a minimum of eight or nine carbon atoms, for example, —(CH$_2$)$_8$— or —(CH$_2$)$_9$— groups.

The acyclic hydrocarbon group contains a maximum of twenty six carbon atoms. Preferably, the acyclic hydrocarbon group independently in each of R$^1$, R$^2$, R$^4$, R$^5$, R$^6$ contains a maximum of four carbon atoms. Preferably, the acyclic hydrocarbon group in X contains a maximum of ten or twelve carbon atoms, for example, —(CH$_2$)$_{10}$— or —(CH$_2$)$_{12}$— groups.

The acyclic hydrocarbon group may be saturated and straight-chained, i.e., a straight-chained alkyl group. Some examples of straight-chained alkyl groups include methyl, ethyl, propyl, butyl, pentyl, hexyl, octyl, nonyl, decyl, dodecyl, hexadecyl, eicosyl, docosyl, and hexacosyl.

Alternatively, the acyclic hydrocarbon group may be saturated and branched, i.e., a branched alkyl group. Some examples of branched alkyl groups include iso-propyl, iso-butyl, sec-butyl, t-butyl, di-(t-butyl)methyl, 3-ethyl-2,3-dimethylhexyl, and 4-(1,1-dimethylethyl)heptyl.

The acyclic hydrocarbon group may alternatively be unsaturated. Unsaturated hydrocarbons include, for example, alkenyl, alkynyl, and combinations thereof, i.e., enynes.

The unsaturated acyclic hydrocarbon group may be straight-chained. Some examples of straight-chained alkenyl groups include vinyl, allyl, 2-butenyl, 3-butenyl, 1-hexenyl, 1,3-hexadienyl, 9-decenyl, 1,3,5-hexatrienyl, oleyl, linolenyl, palmitoleyl, and arachidonyl. Some examples of straight-chained alkynyl groups include acetylenyl, propargyl, and butynyl. Some examples of straight-chained enynes include hex-1-en-3-ynyl and hexa-1,5-dien-3-ynyl.

Alternatively, the unsaturated acyclic hydrocarbon group may be branched. Some examples of branched alkenyl groups include 2-methylene-3-butenyl and 2,3-dimethyl-but-2-enyl. An example of a branched alkynyl group includes 2,5-dimethyl-hex-3-ynyl.

X and Y may also independently represent a ring. The ring may be, for example, a four, five, six, seven, or eight member ring.

The ring may be saturated or unsaturated. An unsaturated ring contains at least one double bond. For example, a five member ring can have one or two double bonds, and a seven member ring can have one to three double bonds.

In one embodiment, the ring is a carbocyclic ring. The carbocyclic ring may be saturated. Some examples of suitable saturated carbocyclic rings include cyclobutane, cyclopentane, cyclohexane, cycloheptane, and cyclooctane rings.

Alternatively, the carbocyclic ring may be unsaturated. The unsaturated carbocyclic rings may be either aromatic, i.e., "aryl" or "arenyl," or non-aromatic.

Examples of unsaturated carbocyclic rings include cyclopentene, cyclohexene, cycloheptene, cyclopentadiene, 1,3-cyclohexadiene, 1,4-cyclohexadiene, 1,3-cycloheptadiene, cycloheptatriene, and cyclooctadiene rings. Preferably, the unsaturated carbocyclic ring is a benzene ring, i.e., phenyl or phenylene.

Any of the acyclic and carbocyclic hydrocarbon groups described above may have one or more carbon atoms substituted by one or more heteroatoms. Some preferred heteroatoms include, for example, nitrogen (N), oxygen (O), sulfur (S), and combinations thereof.

The nitrogen and sulfur heteroatoms may also contain additional substituents. For example, a nitrogen heteroatom may be an amine oxide or oxime. A sulfur heteroatom may be a sulfoxide or sulfone. In addition, where the nitrogen is not double bonded within a ring or an acyclic chain, the nitrogen may be substituted by any suitable group, such as, for example, H and lower alkyl.

Since any of the nitrogen heteroatoms discussed above may be positively charged, any such positively charged nitrogen heteroatoms may contribute to the positive charge (z). Accordingly, a positive charge z of 4, or higher than 4, may be due in part to positively charged nitrogen heteroatoms.

The acyclic and carbocyclic hydrocarbon groups may be substituted with more than one heteroatom as long as the resulting heteroatom-substituted hydrocarbon is stable. The stable heteroatom-substituted acyclic or carbocyclic hydrocarbons do not have one heteroatom bound to another heteroatom. Moreover, no heteroatom is bound to: $V^1$ when $V^1$ is N or $N^+$; $V^2$ when $V^2$ is $N^+$; $V^3$ when $V^3$ is $N^+$; or $V^4$ when $V^4$ is N or $N^+$. Some examples of unstable heteroatom-substituted hydrocarbons not considered herein include hydrazines, peroxides, and disulfides.

The term "lower alkyl" refers to an acyclic hydrocarbon group having one to six carbon atoms. Lower alkyl groups may be branched or unbranched, and saturated or unsaturated. Some examples of saturated lower alkyl groups include methyl, ethyl, n-propyl, isopropyl, n-butyl, sec-butyl, i-butyl, t-butyl, n-pentyl, n-hexyl, 4-methyl-2-pentyl, and so on. Some examples of unsaturated lower alkyl groups include vinyl, propenyl, isopropenyl, propargyl, and so on.

Accordingly, in one embodiment, the acyclic hydrocarbon group is heteroatom-substituted to form a polyalkyleneoxide. Some examples of polyalkyleneoxides include polymethyleneoxide, polyethyleneoxide, polypropylenenoxide, and combinations thereof.

When one or more carbon atoms of the carbocyclic rings described above are substituted by one or more heteroatoms described above, a heterocyclic ring is formed. Accordingly, X and Y may also be heterocyclic rings.

The heterocyclic ring may be saturated. Examples of saturated heterocyclic rings containing one or more nitrogen heteroatoms include pyrrolidine, piperidine, imidazolidine, N,N'-dimethylimidazolidine, pyrazolidine, piperazine, homopiperazine, and hexahydro-1,3,5-triazine rings. Examples of saturated heterocyclic rings containing one or more oxygen heteroatoms include tetrahydrofliran, tetrahydropyran, and 1,4-dioxane rings. Examples of saturated heterocyclic rings containing one or more sulfur heteroatoms include tetrahydrothiophene and 1,4-dithiane rings. Examples of saturated heterocyclic rings containing a combination of heteroatoms include 1,3-oxazolidine, 1,3-thiazolidine, 1,3-oxathiolane, and morpholine rings.

Alternatively, the heterocyclic ring may be unsaturated. The unsaturated heterocyclic rings may be either aromatic, i.e., "heteroaryl" or "heteroarenyl," or non-aromatic.

Examples of unsaturated heterocyclic rings containing one or more nitrogen heteroatoms include pyrrole, pyridine, pyrazole, pyrazine, pyrimidine, imidazole, and triazine rings. Examples of unsaturated heterocyclic rings containing one or more oxygen heteroatoms include furan, pyran, and 1,3-dioxole rings. Examples of unsaturated heterocyclic rings containing one or more sulfur heteroatoms include thiophene, thiopyran, 1,3-dithiole, and 1,3-dithiine rings. Examples of unsaturated heterocyclic rings containing a combination of heteroatoms include oxazole, thiazole, and oxathiole rings.

Any of the carbocyclic and heterocyclic rings for X and Y described above may also be polycyclic. Some examples of polycyclic carbocyclic ring systems include bicyclo[2.2.2]octane and bicyclo[3.3.3]undecane. Some examples of polycyclic heterocyclic ring systems include 1,4-diazabicyclo[2.2.2]octane, 1-aza-4-azonia-bicyclo[2.2.2]octane, 1,4-diazoniabicyclo[2.2.2]octane, 1,5-diaza-bicyclo[3.3.3]undecane, 1-aza-5-azonia-bicyclo[3.3.3]undecane, and 1,5-diazaoniabicyclo[3.3.3]undecane.

In addition, any of the carbocyclic and heterocyclic rings described above may be fused to one or more, typically one or two, other rings to make a fused ring system.

In one embodiment, the fused rings are all carbocyclic and saturated. Some examples of such fused ring systems include decahydronaphthalene, tetradecahydroanthracene, tetradecahydrophenanthrene and hexadecahydropyrene fused rings. In another embodiment, the carbocyclic fused ring system is composed of a combination of saturated and unsaturated rings. Some examples of such fused ring systems include bicyclo[4.3.0]non-3-ene, bicyclo[4.4.0]dec-8-ene, and bicyclo[4.4.0]dec-7,9-diene fused rings.

In another embodiment, all of the fused carbocyclic rings are unsaturated. The unsaturated carbocyclic rings may also be aromatic. Some examples of unsaturated carbocyclic fused ring systems which are also aromatic include naphthalene, phenanthrene, anthracene, triphenylene, azulene, chrysene, pyrene, and biphenylene fused rings.

In yet another embodiment, the fused ring system is composed of a mixture of carbocyclic and heterocyclic rings. Some examples of such fused ring systems include indoline, quinoline, isoquinoline, phthalazine, benzimidazole, benzothiazole, benzisoxazole, benzodioxole, quinoxaline, quinazoline, benzoxazine, cinnoline, acridine, and phenazine fused rings.

In yet another embodiment, the fused ring system is composed of only heterocyclic rings. Examples of such fused ring systems include pteridine, purine, 1,8-naphthyridine, 1,8,9-triazaanthracene, 1,5-diazabicyclo[4.3.0]non-5-ene and thieno[3,2-b]furan fused rings.

In formula (1), X and Y may also independently represent a combination of any of the ring or fused ring systems described above and any of the acyclic hydrocarbon groups described above. For example, the foregoing groups may represent a combination of an alkyl or alkenyl group with an aryl or heteroaryl ring.

Some examples of such combination groups for X include benzyl ($—CH_2—C_6H_4—$), O-tolyl ($—C_6H_5$-o-$CH_2—$), o-xylyl (o-$CH_2—C_6H_4—CH_2—$), m-xylyl (m-$CH_2—C_6H_4—CH_2—$), p-xylyl (p-$CH_2—C_6H_4—CH_2—$), dimethylpyridinyl, e.g., lutidinyl ($—CH_2—(NC_5H_3)—CH_2—$), and dimethylpyrazinyl (e.g., $—CH_2—(NC_4H_2N)—CH_2—$). Some examples of such combination groups for Y include benzyl ($—CH_2—C_6H_5$), o-tolyl ($—C_6H_5$-o-$CH_3$), o-xylyl (o-$CH_2—C_6H_4—CH_3$), m-xylyl (m-$CH_2—C_6H_4—CH_3$), p-xylyl (p-$CH_2—C_6H_4—CH_3$), methylpyridinyl ($—CH_2—(NC_5H_4)$), and N-methylpyrazinyl ($—NC_4H_4N—CH_3$).

Additional examples of combination groups suitable for X or Y include 1,2-dimethylphenyl, 1,2-dimethylphenylene, 1,4-diisopropylphenyl, 1,4-dimethylphenylene, 1,2-dimethylbenzyl, cumenyl, 2-methylpyridinyl, 2-ethylpyrazinyl, 2-methylimidazolyl, and 2-propylbenzimidazole.

Any of the groups thus far described may be either unsubstituted, or substituted with one or more substituents. Some examples of substituents include $—OR^7$, $—N(R^7)_2$, $—C(O)N(R^7)_2$, $—SR^7$, halo, and $—COOR^7$. Halo includes, for example, F, Cl, and Br. $R^7$ independently represents H, phenyl, or a lower alkyl group as previously defined.

In formula (1), $V^1$ and $V^4$ independently represent C, N, or $N^+$, and $V^2$ and $V^3$ independently represent C or $N^+$. The subscript m1 represents the presence or absence of the Y group bound to $V^1$. The subscript m2 represents the presence or absence of the Y group bound to $V^4$. The subscript m3 represents the presence or absence of the polycyclic ring system containing $V^3$ and $V^4$. The subscripts m1, m2, and m3 independently represent 1 when any of the mentioned groups are present, or represent 0 when any of the mentioned groups are absent.

When $V^1$ represents C or $N^+$, any one of $R^1$, $R^2$, or $R^3$ may be bound to the C or $N^+$ with a double bond. In such a case, $V^1$ may be C or $N^+$ without requiring $V^1$ to be bound to Y, i.e., m1 in $(Y)_{m1}$ is 0. Similarly, when $V^4$ represents C or $N^+$, $V^4$ does not require a bond to Y if any one of $R^4$, $R^5$, or $R^6$ is bound to V4 with a double bond, i.e., m2 in $(Y)_{m2}$ would be 0.

However, preferably, when $V^1$ represents C or $N^+$, then none of $R^1$, $R^2$, or $R^3$ is bound to $V^1$ with a double bond, and thus, m1 in $(Y)_{m1}$ is 1 when $V^1$ represents C or $N^+$. Similarly, it is preferable that when $V^4$ represents C or $N^+$, then none of $R^4$, $R^5$, or $R^6$ is bound to V4 with a double bond, and thus, m2 in $(Y)_{m2}$ is 1 when $V^2$ represents C or $N^+$.

In one embodiment of formula (1), m3 is 0. When m3 is 0, then X is a non-linking group. Accordingly, when m3 is 0, the ion may be represented by formula (1a) below. In formula (1a), $R^1$, $R^2$, $R^3$, X, Y, z, and m1 are as previously defined.

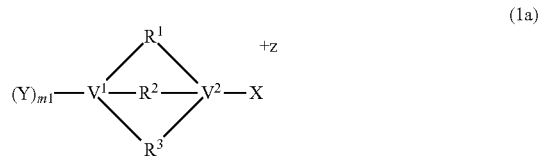
(1a)

In a further embodiment to formula (1a), one of $V^1$ and $V^2$ represents $N^+$, z represents 1, and $m^1$ is 0. For example, $V^1$ may represent N and $V^2$ may represent N as shown in formula (1k) below:

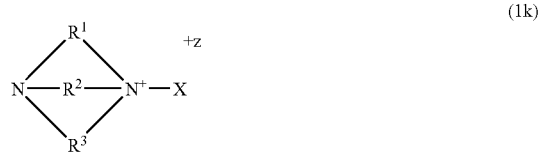
(1k)

In a further embodiment to formula (1k), $R^1$, $R^2$, and $R^3$ are independently represented by the formula $C_nH_{2n}$. Preferably, n represents an integer from 1 to 10. More preferably, n represents an integer from 1 to 3. Even more preferably, n is 2 in the formula $C_nH_{2n}$ for all three of $R^1$, $R^2$, and $R^3$, as shown in formula (1m) below:

(1m)

In formula (1m), X represents preferably an acyclic hydrocarbon group having one to twenty six carbons atoms. More preferably, X represents an acyclic hydrocarbon group having ten to eighteen carbon atoms. Even more preferably, X represents an acyclic hydrocarbon group having twelve to sixteen carbon atoms. Some particularly preferred ions are given below in formulas (1n) and (1p).

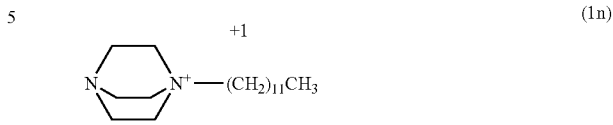
(1n)

1-aza-4-azonia-4-dodecylbicyclo[2.2.2]octane (positively charged ion component of JE188)

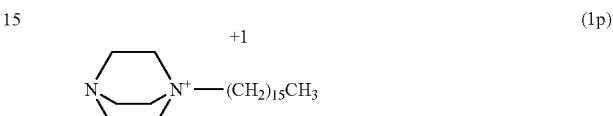
(1p)

1-aza-4-azonia-4-hexadecylbicyclo[2.2.2]octane (positively charged ion component of TA279)

In another embodiment of formula (1), m3 is 1. When m3 is 1, then X is a linking group. Accordingly, in one embodiment, when m3 is 1, the ion may be represented by the generic formula (1b):

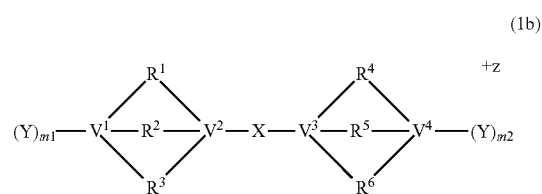
(1b)

In formula (1b), $R^1$, $R^2$, $R^3$, $R^4$, $R^5$, $R^6$, X, Y, $V^1$, $V^2$, $V^3$, $V^4$, m1, m2, and z are as previously defined.

In formula (1b), $V^1$ and $V^2$ may both represent $N^+$, and $V^3$ and $V^4$ may both represent C. A representative formula in accordance with the foregoing embodiment is given as formula (1c):

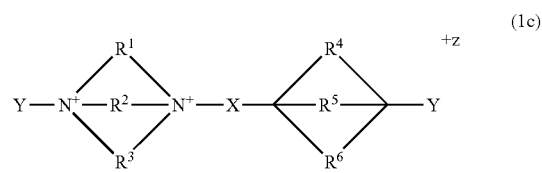
(1c)

Alternatively, $V^1$ and $V^2$ may both represent $N^+$, while $V^3$ represents C and $V^4$ represents N. A representative formula in accordance with the foregoing embodiment is given as formula (1d):

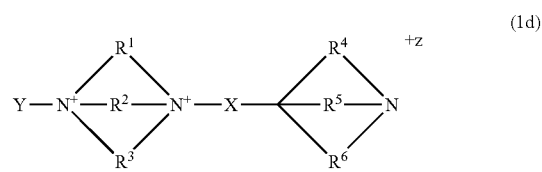
(1d)

In formula (1b), $V^1$ and $V^3$ may both represent $N^+$, and $V^2$ and $V^4$ may both represent C. A representative formula in accordance with the foregoing embodiment is given as formula (1e):

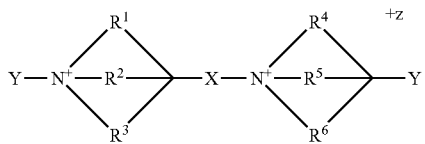
(1e)

Alternatively, $V^1$ and $V^3$ may both represent $N^+$, while $V^2$ represents C and $V^4$ represents N. A representative formula in accordance with the foregoing embodiment is given as formula (1f):

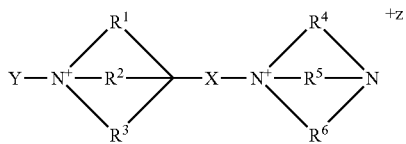
(1f)

In formula (1b), $V^1$ and $V^4$ may both represent $N^+$, and $V^2$ and $V^3$ may both represent C. A representative formula in accordance with the foregoing embodiment is given as formula (1g):

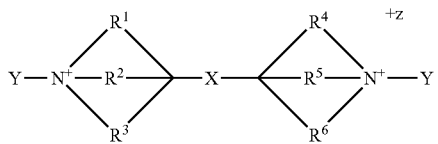
(1g)

In formula (1b), $V^2$ and $V^3$ may both represent $N^+$, and $V^1$ and $V^4$ may both represent C. A representative formula in accordance with the foregoing embodiment is given as formula (1h):

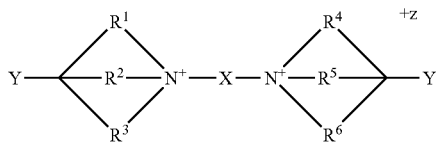
(1h)

Alternatively, $V^2$ and $V^3$ may both represent $N^+$, while $V^1$ represents C and $V^4$ represents N. A representative formula in accordance with the foregoing embodiment is given as formula (1i):

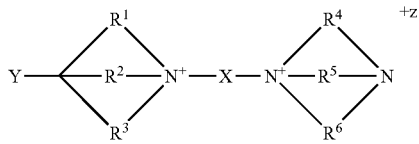
(1i)

In formula (1b), $V^1$, $V^2$ and $V^3$ may all represent $N^+$, while $V^4$ represents C. A representative formula in accordance with the foregoing embodiment is given as formula (1j):

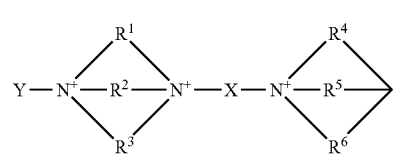
(1j)

Alternatively, $V^2$ and $V^3$ may both represent $N^+$, while $V^1$ and $V^4$ independently represent N or $N^+$. A representative formula in accordance with the foregoing embodiment is given as formula (2):

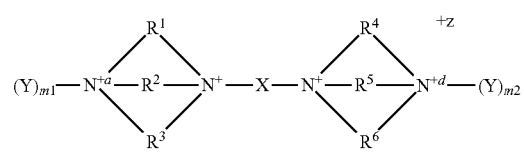
(2)

In formula (2) above, $R^1$, $R^2$, $R^3$, $R^4$, $R^5$, $R^6$, X, Y, m1, and m2 are as previously defined. The superscripts a and d independently represent 0 or 1.

In a preferred embodiment, each of $R^1$, $R^2$, $R^3$, $R^4$, $R^5$, and $R^6$ in formula (2) above are independently represented by the formula $C_nH_{2n}$, wherein n represents an integer from 1 to 26. More preferably, n is an integer from 1 to 10. Even more preferably, n is an integer from 1 to 4. Even more preferably, n is an integer from 1 to 3. Even more preferably, n is 2 in the formula $C_nH_{2n}$ for all six of $R^1$, $R^2$, $R^3$, $R^4$, $R^5$ and $R^6$. A representative formula in accordance with the foregoing embodiment is given as formula (3):

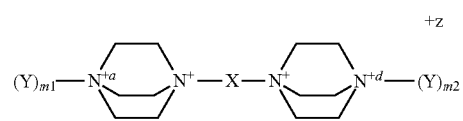
(3)

In a further preferred embodiment of formula (3), a and d are both 0 and m1 and m2 are both 0. In the foregoing embodiment, each bicyclic ring system in formula (3) represents a 4-aza-1-azoniabicyclo[2.2.2]octane ring system. A representative formula in accordance with the foregoing embodiment is given as formula (3a):

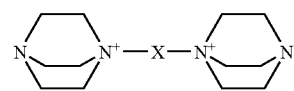
(3a)

In a further preferred embodiment of formula (3a), X represents an acyclic hydrocarbon group as previously defined. In a preferred embodiment, the acyclic hydrocarbon group for X has four to twelve carbon atoms. For example, some particularly preferred hydrocarbon groups for X include —$(CH_2)_8$—, —$(CH_2)_9$—, —$(CH_2)_{10}$—, and —$(CH_2)_{12}$—.

Accordingly, some particularly preferred ions are represented by the following formulas:

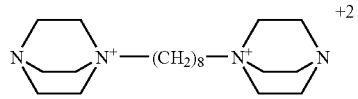

1,8-[bis(4-aza-1-azoniabicyclo[2.2.2]octanyl)]octane

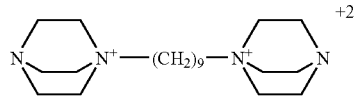

1,9-[bis(4-aza-1-azoniabicyclo[2.2.2]octanyl)]nonane

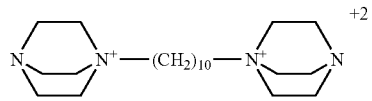

1,10-[bis(4-aza-1-azoniabicyclo[2.2.2]octanyl)]decane

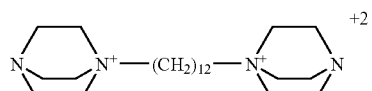

1,12-[bis(4-aza-1-azoniabicyclo[2.2.2]octanyl)]dodecane

In another preferred embodiment of formula (3a), X contains a phenylene ring. Particularly preferred phenylene-containing groups for X include the xylyl groups. A representative formula in accordance with the foregoing embodiment is given as formula (4):

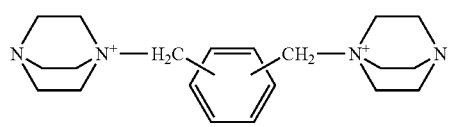

In a particularly preferred ion of formula (4), X represents p-xylyl. The ion, α,α'-[bis(4-aza-1-azoniabicyclo[2.2.2]octanyl)]p-xylene, corresponds to the following formula (5):

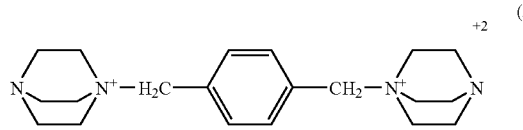

In another embodiment of formula (3), $V^1$, $V^2$ and $V^3$ all represent $N^+$, while $V^4$ represents N. A representative formula in accordance with the foregoing embodiment is given as formula (6):

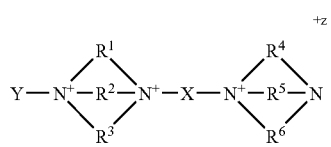

In another embodiment of formula (3), all of $V^1$, $V^2$, $V^3$, and $V^4$ represent $N^+$. A representative formula in accordance with the foregoing embodiment is given as formula (7):

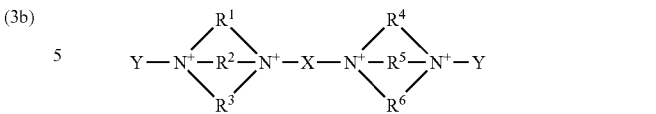

For the purpose of clarity, the ion shown in any of the formulas thus far shown may be ascribed the symbol (I). The ion (I) according to any of these formulas requires, by necessity, to be associated with a negatively charged counteranion or counteranions (W) to make a neutral compound.

Any counteranion may be useful for the purposes of the present invention. A particular counteranion may be chosen for any number of reasons including its optimizing effect on the function of the ion, and/or its effect on solubility, density, ease of manufacture, cost, and so on, of the compound that includes the ion.

The counteranion may be singly negatively charged, i.e., a simple counteranion. Some examples of suitable simple counteranions include chloride, perchlorate, sulfate, nitrate, and tetrafluoroborate.

Alternatively, the counteranion may be, for example, doubly negatively or triply negatively charged, i.e., a dianion or trianion. Some examples of suitable counter dianions include carbonate, oxide, sulfide, oxalate, fumarate, terephthalate, malonate, maleate, succinate, catecholate, ascorbate, and a doubly deprotonated porphyrin. Some examples of suitable counter trianions include phosphate, citrate, ascorbate, 1,3,5-benzenetricarboxylate, 1,3,5-benzenetriolate, 2-carboxymalonate, and erythritolate.

From the above, it is evident that numerous ion-counteranion combinations are possible. Accordingly, the ion-counteranion combinations are appropriately described by the following formula:

$$[I^{+z}]_u[W^{-r}]_t \qquad (8)$$

In formula (8), the symbol I represents an ion of the present invention in accordance with any of the formulas thus far shown. W represents any suitable counteranion, such as those described above. z is the charge of the ion as previously described. r is the charge of the counteranion. By the rules of chemistry, counter charges are balanced in formula (8) according to the formula uz=rt.

Method for Modulating

In another aspect, the present invention provides a method for modulating potassium, sodium and cyclic nucleotide-modulated ion channels in a mammal in need thereof. The method comprises administering to the mammal an effective amount of an ion as described above.

In one embodiment, the ion channel is a potassium ion channel. Any type of potassium ion channel may be modulated in accordance with the method of the present invention. Examples of potassium ion channels include pore-forming α-subunit channels with or without modulatory β-subunits.

The pore-forming α-subunit group of potassium channels typically contains either 1) six transmembrane segments and one pore-forming region, 2) two transmembrane segments and one pore-forming region, or 3) four transmembrane segments and two pore-forming regions. The α-subunit group can be further sub-divided based on the channels defining property (e.g., voltage-gated, calcium-activated, inward, rectifier, ATP-sensitive, etc.) and sequence similarity (e.g., Kv1.1, Kv1.2, etc.). Examples of pore-forming α-subunit potassium channels are shown below in Table 1.

The non pore-forming (modulatory) β-subunit group of potassium channels includes single transmembrane spanning proteins, such as Mink and Mink-related proteins (MiRPs), and large ATP-binding cassette (ABC) transport-related proteins, such as the sulfonylurea receptors. Examples of modulatory β-subunits are shown below in Table 2.

A potassium ion channel comprising any of the subunits shown in Table 1 and Table 2 can be modulated in accordance with the method of the present invention.

In another embodiment, the ion channel is a sodium ion channel. Any type of sodium ion channel can be modulated in accordance with the method of the present invention. An example of a class of sodium channel useful in the method of the present invention is the voltage-gated sodium channel. Examples of voltage-gated sodium channels include $Na_v1.1$, $Na_v1.2$, $Na_v1.3$, $Na_v1.4$, $Na_v1.5$, $Na_v1.6$, $Na_v1.7$, $Na_v1.8$ and $Na_v1.9$.

Another example of a class of sodium channel useful in the method of the present invention is the epithelia sodium channels (ENaC). Any epithelia sodium channel known to those in the art can be modulated in accordance with the method of the invention. For example, the epithelial sodium channel can comprise an alpha, beta, gamma and/or delta subunit.

In yet another embodiment, the ion channel is a cyclic nucleotide-modulated ion channel. Any type of cyclic nucleotide-modulated ion channel may be modulated in accordance with the method of the present invention. Examples of cyclic nucleotide-modulated ion channels include the cyclic nucleotide gated (CNG) channels and the hyperpolarization-activated cyclic nucleotide gated channels (HCN).

Examples of CNG channels include CNGA1, CNGA2, CNGA3, CNGA4, CNGB1 and CNGB3. Examples of HCN channels include HCN1, HCN2, HCN3 and HCN4.

TABLE 1

Pore-forming K⁺ channel α-subunits

| Subclass | Channel | Gene |
|---|---|---|
| Six transmembrane domains, one pore | | |
| Voltage-gated (shaker) | Kv1.1 | KCNA1 |
| | Kv1.2 | KCNA2 |
| | Kv1.3 | KCNA3 |
| | Kv1.4 | KCNA4 |
| | Kv1.5 | KCNA5 |
| | Kv1.6 | KCNA6 |
| | Kv1.7 | KCNA7 |
| Voltage-gated (shab) | Kv2.1 | KCNB1 |
| | Kv2.2 | KCNB2 |
| Voltage-gated (shaw) | Kv3.1 | KCNC1 |
| | Kv3.2 | KCNC2 |
| | Kv3.3 | KCNC3 |
| | Kv3.4 | KCNC4 |
| Voltage-gated (shal) | Kv4.1 | KCND1 |
| | Kv4.2 | KCND2 |
| | Kv4.3 | KCND3 |
| Voltage-gated (silent) | Kv5.1 | KCNE1 |
| | Kv6.1 | KCNG1 |
| | Kv6.2 | KCNG2 |
| | Kv6.3 | KCNG3 |
| | Kv8.1 | |
| | Kv9.2 | KCNS1 |
| | Kv9.2 | KCNS2 |
| | Kv9.3 | KCNS3 |
| Voltage-gated (EAG) | EAG | KCNH1 |
| | EAG2 | |
| | ERG1 | KCNH2 |
| | ERG2 | |
| | ERG3 | |
| | ELK1 | KCNH4 |
| | ELK2 | KCNH3 |
| | ELK3 | |

TABLE 1-continued

Pore-forming K⁺ channel α-subunits

| Subclass | Channel | Gene |
|---|---|---|
| Voltage-gated (KvLQT related) | KCNQ1 | KCNQ1 |
| | KCNQ2 | KCNQ2 |
| | KCNQ3 | KCZQ3 |
| | KCNQ4 | KCNQ4 |
| | KCNQ5 | KCNQ5 |
| $Ca^{2+}$-activated (large conductance) | Slo-1 | KCNMA1 |
| | Slo-2 | KCNMA2 |
| | Slo-3 | KCNMA3 |
| $Ca^{2+}$-activated (intermediate conductance) | IKCA | KCNN4 |
| $Ca^{2+}$activated (small conductance) | SK1 | KCNN1 |
| | SK2 | KCNN2 |
| | SK3 | KCNN3 |
| Two transmembrane domains, one pore | | |
| Inward rectifier (ROMK1) | Kir1.1 | KCNJ1 |
| Inward rectifier | Kir2.1 | KCNJ2 |
| | Kir2.2 | KCNJ12 |
| | Kir2.3 | KCNJ4 |
| | Kir2.4 | KCNJ14 |
| Inward rectifier (G-protein regulated) | Kir3.1 | KCNJ3 |
| | Kir3.2 | KCNJ6 |
| | Kir3.3 | KCNJ9 |
| | Kir3.4 | KCNJ5 |
| Inward rectifier | Kir4.1 | KCNJ10 |
| | Kir4.2 | KCNJ15 |
| | Kir5.1 | KCNJ16 |
| | Kir7.1 | KCNJ13 |
| Inward rectifier (ATP sensitive) | Kir6.1 | KCNJ8 |
| | Kir6.2 | KCNJ11 |
| Four transmembrane domains, two pores | | |
| Two Pore | TWIK-1 | KCNK1 |
| | TWIK-2 | KCNK6 |
| | KCNK7 | KCNK7 |
| | TASK | KCNK3 |
| | TASK-2 | KCNK5 |
| | TASK-3 | KCNK9 |
| | TASK-5 | KCNK15 |
| | TRAAK | KCNK4 |
| | TREK-1 | KCNK2 |
| | TREK-2 | KCNK10 |
| | THIK-1 | KCNK13 |
| | THIK-2 | KCNK12 |
| | TALK-1 | KCNK16 |
| | TALK-2 | KCNK17 |

TABLE 2

Modulatory K⁺ channel β-subunits

| Name | Known partners | Gene |
|---|---|---|
| MinK | KCNQ1, ERG1 | KCNE1 |
| Mirp1 | ERG1, KCNQ2, KCNQ3, Kv4.2 | KCNE2 |
| Mirp2 | KCNQ1, KCNQ4, Kv3.4 | KCNE3 |
| Mirp3 | | KCNE4 |
| Bkβ1 | Slo-1 | KCNMB1 |
| BKβ2 | Slo-1 | KCNMB2 |
| BKβ3 | Slo-1 | KCNMB3 |
| BKβ4 | Slo-1 | KCNMB4 |
| Kvβ1 | Kv1.x | |
| Kvβ2 | Kv1.x | KCNAB1 |
| Kvβ3 | Kv1.x | KCNAB2 |
| KCHIP1 | Kv4.x | KCNIP1 |
| KCHIP2 | Kv4.x | KCNIP2 |
| KCHIP3 | Kv4.x | |
| KCHAP | Kv2.1, Kv4.3 | |
| SUR1 | Kir6.1, Kir6.2 | ABCC8 |
| SUR2 | Kir6.1, Kir6.2 | ABCC9 |

In a further aspect, the present invention provides a method for modulating a ligand-gated ion channel and transient receptor potential (Trp) ion channel in a mammal in need thereof. The method comprises administering to the mammal an effective amount of an ion as described above.

In one embodiment, the ion channel is a ligand-gated ion channel. Any type of ligand-gated ion channel may be modulated in accordance with the method of the present invention. Examples of ligand-gated channels include cys-loop ligand gated ion channels, ATP gated ion channels, and glutamate activated cationic channels.

Any Cys-loop ligand gated ion channel can be modulated in accordance with the method of the present invention. The cys-loop ligand gated ion channels can be cation specific or anion specific. Examples of cation specific cys-loop ligand gated ion channels include nicotinic receptors, 5-hydroxytryptamine receptor type 3 receptors, and the zinc activated ion channel. Examples of anion specific cys-loop ligand gated ion channels include γ-aminobutyric acid type A ($GABA_A$, which includes ρ subunits sometimes referred to as $GABA_C$), and glycine receptors.

Any ATP gated ion channel can be modulated in accordance with the method of the present invention. Examples of ATP gated ion channel include ATP2x receptors and CFTR.

Any glutamate activated cationic channel can be modulated in accordance with the method of the present invention. Examples of glutamate activated cationic cationic channels include NMDA receptors, AMPA receptors, and Kainate receptors.

In another embodiment, the ion channel is a transient receptor potential (Trp) ion channel. Any type of Trp ion channel may be modulated in accordance with the method of the present invention. Examples of Trp ion channels include Trpc (e.g., Trpc1, Trpc2, Trpc3, Trpc4, Trpc5 Trpc6, Trpc7, etc.), Trpv (e.g., Trpv1, Trpv2, Trpv3, Trpv4, Trpv5, Trpv6, etc), Trpm (e.g., Trpm1, Trpm2, Trpm3, Trpm4, Trpm5, Trpm6, Trpm7, Trpm8, etc), ANKTM1, Trpp (e.g., Trpp2, Trpp3, Trpp5, etc), and Trpml (e.g., Troml1, Trpml2, Trpml3, etc).

Administration

In one aspect of the invention, the effective amount of an ion administered in accordance with the method of the invention is any amount effective for modulating a potassium, sodium, or cyclic nucleotide-modulated ion channel. In another aspect of the invention, the effective amount of an ion administered in accordance with the method of the invention is any amount effective for modulating a ligand-gated ion channel (e.g., cys-loop ligand gated, ATP gated, glutamate activated cationic gated) or Trp ion channel. An ion is considered to modulate the ion channel if the ion opens, or conversely blocks, the ion channel.

In one embodiment, the administered ion opens an ion channel. The term "open" as used herein refers to an increase of current through an ion channel. The increase in current may be any statistically significant increase occurring upon ion administration. For example, the increase in current may be at least about 10%, preferably at least about 25%, more preferably at least about 50%, even more preferably at least about 75%, and even more preferably at least about 90%. In a preferred embodiment, the administered ion opens an ion channel in a mammal suffering from a disease or condition which would benefit from opening of the ion channel, i.e., from increased current through the channel.

In another embodiment, the administered ion blocks the ion channel. The term "block" as used herein refers to the physical occlusion of the ion channel pore by the ion of the invention, thereby inhibiting current flow. The inhibition of current may be any statistically significant decrease of current occurring upon ion administration. For example, the current flow may be inhibited by at least about 10%, preferably at least about 25%, more preferably at least about 50%, even more preferably at least about 75%, and even more preferably at least about 90%. Optimally, the ion blocks an ion channel in a mammal suffering from a disease or condition which would benefit from a blocked ion channel.

In one aspect of the invention, mammals in need of modulating ion channels are those mammals suffering from a disease or condition characterized by aberrant potassium, sodium, or cyclic nucleotide-modulated ion channel activity. In another aspect of the invention, mammals in need of modulating ion channels are those mammals suffering from a disease or condition characterized by aberrant ligand-gated ion channels or Trp ion channels. Such diseases and conditions are well known to those skilled in the art.

Examples of such diseases or conditions include, but are not limited to, cardiovascular diseases and conditions, immune system diseases and conditions, smooth muscle disorders, central and peripheral nervous system diseases and disorders, skeletal muscle diseases and disorders, endocrine disorders (e.g., disorders associated with hormone secretion), and cell proliferative disorders, and degenerative disorders.

Other diseases and conditions include hyper-reflexic bladder conditions, baldness, deafness, headaches, anxiety, and aberrant excitability in afferents sensitized by chronic inflammation.

Examples of cardiovascular diseases and conditions include long QT syndrome, Brugada syndrome, arrhythmia, atrial fibrillation, atrial flutter, Torsades de Pointes, heart failure, congestive heart failure, ischemia, ventricular fibrillation, ventricular tachycardia and coronary artery disease.

Examples of immune system diseases and conditions include delayed type-hypersensitivity, autoimmune disorders, autoimmune encephalomyelitis, immunosuppression, diseases and conditions characterized by immune cell activation and/or proliferation. Immunosuppression includes the suppression of the immune system via, for instance, administration of therapeutic agents, such as is generally used in organ transplantation.

Examples of nervous system diseases and conditions include stroke, cerebral ischemia, dementia, cognition disorders, sleep disorders, depression, musculoskeletal conditions, epilepsy, Alzheimer's disease, Parkinson's disease, and abnormal regulation of neuronal excitability.

Examples of smooth muscle disorders include hypertension, angina, asthma, urinary incontinence, premature labor, and hypoxia. The hypertension can be any type of hypertension. For example, the hypertension can be pulmonary hypertension, cardiovascular hypertension, and hypertension of the kidneys.

Examples of hormones which can contribute to an endocrine disorder include insulin, prolactin, growth hormone, and cholecystokinin. For example, a disorder involving the hormone insulin is diabetes.

Examples of cell proliferative disorders include cancer, fibrosis, atherosclerosis and restenosis.

Another disease includes cystic fibrosis. For example the ATP gated ion channel, CFTR is reported to be involved in cystic fibrosis.

Trp channels are involved in sensory transduction (e.g., temperature, touch, pain, taste, hearing, etc.) and a variety of other physiological functions. Examples of conditions associated with aberrant Trp channel function include glomerulosclerosis and polycystic kidney disease.

Effective amounts of an ion to be administered are those amounts which are capable of modulating potassium, sodium, or cyclic nucleotide-modulated ion channels. Optimally, such amounts impart a beneficial effect on the mammal.

The administered amount of an ion will vary according to numerous factors that are well known in the art, such as the particular ion utilized, the mode of application, particular subject to be treated, the disease or condition to be treated, etc. The appropriate amount of the ion can readily be determined by those skilled in the art during preclinical and clinical trials.

The minimum amount of an ion administered to a mammal is the lowest amount capable of modulating a potassium, sodium, or cyclic nucleotide-modulated channel. The maximum amount administered to a mammal is the highest effective amount that does not cause undesirable side effects.

Any mammal can be treated in accordance with the method of the present invention. Mammals include, for example, humans, baboons, and other primates, as well as pet animals such as dogs and cats, laboratory animals such as rats and mice, and farm animals such as horses, sheep and cows.

An ion useful in the method of the present invention may be administered by any method known in the art. Some examples of suitable modes of administration include oral and systemic administration. Systemic administration can be enteral or parenteral, e.g., administered intravenously; intramuscularly; subcutaneously, as injectable solutions or suspensions; intraperitoneally; or rectally. Liquid or solid (e.g., tablets, gelatin capsules) formulations can be employed.

An ion may be administered to a mammal by controlled release, as is known in the art. Controlled release administration is a method of drug delivery to achieve a certain level of the drug over a particular period of time. The level of ion over a particular period of time is typically measured by plasma or serum concentrations. Suitable controlled release formulations include delayed, sustained, and immediate (i.e., instantaneous) release. Methods for controlled release of compounds are well known in the art, and are described in, for example, international patent application PCT/US02/10748, and U.S. Pat. Nos. 5,567,439; 6,838,094; 6,863,902; and 6,905,708.

Other routes of administration include oral, topical, intrabronchial, or intranasal administration. For oral administration, liquid or solid formulations may be used. Some examples of formulations suitable for oral administration include tablets, gelatin capsules, pills, troches, elixirs, suspensions, syrups, and wafers. Intrabronchial administration can include an inhaler spray. For intranasal administration, administration of an ion can be accomplished by a nebulizer or liquid mist.

The ion can be formulated in a suitable pharmaceutical carrier. In this specification, a pharmaceutical carrier is considered to be synonymous with a vehicle or an excipient as is understood by practitioners in the art. Examples of carriers include starch, milk, sugar, certain types of clay, gelatin, stearic acid or salts thereof, magnesium or calcium stearate, talc, vegetable fats or oils, gums and glycols.

The ion can be formulated into a composition containing one or more of the following: a stabilizer, a surfactant, preferably a nonionic surfactant, and optionally a salt and/or a buffering agent.

The stabilizer may, for example, be an amino acid, such as for instance, glycine; or an oligosaccharide, such as for example, sucrose, tetralose, lactose or a dextran. Alternatively, the stabilizer may be a sugar alcohol, such as for instance, mannitol; or a combination thereof. Preferably the stabilizer or combination of stabilizers constitutes from about 0.1% to about 10% weight for weight of the ion.

The surfactant is preferably a nonionic surfactant, such as a polysorbate. Some examples of suitable surfactants include Tween 20, Tween 80; a polyethylene glycol or a polyoxyethylene polyoxypropylene glycol, such as Pluronic F-68 at from about 0.001% (w/v) to about 10% (w/v).

The salt or buffering agent may be any salt or buffering agent. Suitable salts include, for example, sodium or potassium chloride. Suitable buffers include, for example, sodium or potassium bicarbonate or biphosphate. Preferably, the buffering agent maintains the pH of the ion formulation in the range of about 5.5 to about 7.5. The salt and/or buffering agent is also useful to maintain the osmolality at a level suitable for administration to a mammal. Preferably the salt or buffering agent is present at a roughly isotonic concentration of about 150 mM to about 300 mM.

The ion can be formulated into a composition which may additionally contain one or more conventional additives. Some examples of such additives include a solubilizer such as, for example, glycerol; an antioxidant such as for example, benzalkonium chloride (a mixture of quaternary ammonium compounds, known as "quart"), benzyl alcohol, chloretone or chlorobutanol; anaesthetic agent such as for example a morphine derivative; or an isotonic agent etc., such as described above. As a further precaution against oxidation or other spoilage, the composition may be stored under nitrogen gas in vials sealed with impermeable stoppers.

Examples have been set forth below for the purpose of illustration and to describe the best mode of the invention at the present time. However, the scope of this invention is not to be in any way limited by the examples set forth herein.

EXAMPLES

Example 1

Representative Syntheses of Didabco Compounds

Dabco was purchased from Sigma-Aldrich Co. (St. Louis, Mo.). Generally, dabco is taken in reaction with a suitably functionalized haloalkane in an inert solvent; such as ethanol, unless limited reaction on the dabco is desired in which instances ethyl acetate is used.

Three structural classes of dabco derivatives were synthesized. Members of structural class A bear a lipophilic chain of variable length attached through one of the nitrogens of dabco (see schematic 1).

Schematic 1

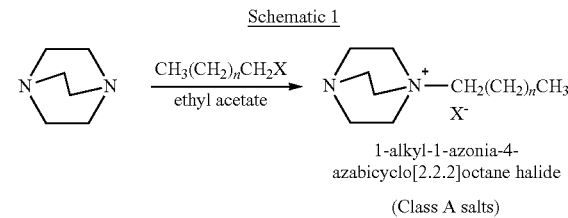

1-alkyl-1-azonia-4-azabicyclo[2.2.2]octane halide (Class A salts)

In schematic 1, limited reaction of dabco with a single equivalent of an appropriately substituted 1-haloalkane in ethyl acetate was performed followed by capping with the desired simple terminal haloalkane.

Members of Structural Class B contain two dabco units with a hydrocarbon spacer (see schematic 2).

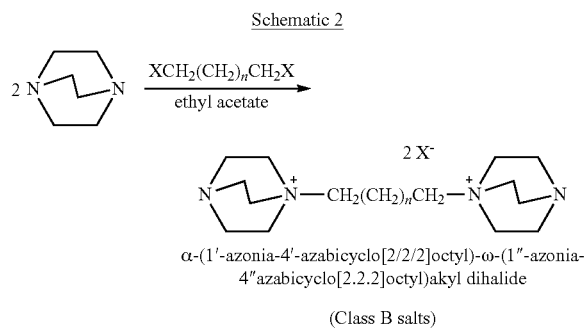

Schematic 2

α-(1'-azonia-4'-azabicyclo[2/2/2]octyl)-ω-(1"-azonia-4"azabicyclo[2.2.2]octyl)akyl dihalide (Class B salts)

In schematic 2, a didabco species was first generated by reaction of an excess of dabco in ethyl acetate with the appropriate α,ω-dihaloalkane. The resultant material was then taken sequentially in limited reaction with a single equivalent of an appropriately substituted 1-haloalkane in ethyl acetate followed by capping with the desired simple terminal haloalkane.

Members of Structural Class C contain two dabco units separated by carbon chains and an aromatic ring, with the substituents of the aromatic ring being in ortho-, meta- and para-relationships (see schematic 3).

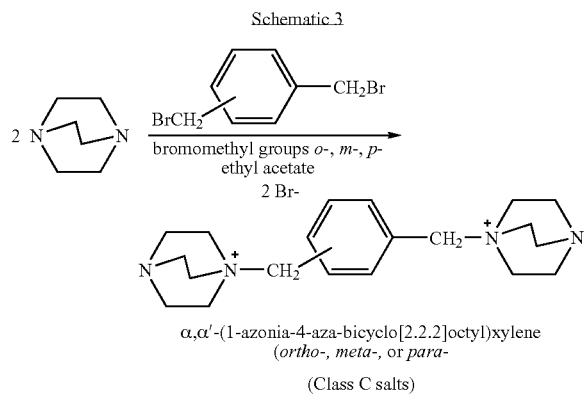

Schematic 3

α,α'-(1-azonia-4-aza-bicyclo[2.2.2]octyl)xylene
(ortho-, meta-, or para- (Class C salts)

In schematic 3, the procedure is similar to that of schematic 2. In schematic 3, the reaction starts with the ortho, meta, and para-bis(halomethyl)benzene reagents.

Synthesized compounds were determined to be pure due to the lack of detectable contaminants by NMR analysis.

For example, a didabco compound containing the ion corresponding to formula (3b), i.e., 1,8-[bis(4-aza-1-azoniabicyclo[2.2.2]octanyl)]octane, was prepared as follows: Two equivalents of DABCO (1,4-diazabicyclo[2.2.2]octane) was dissolved in 100 mL of acetonitrile with stirring at room temperature. To the DABCO solution was added one equivalent of 1,8-dichlorooctane while stirring. The resulting reaction mixture was stirred at room temperature for one day, forming a white precipitate. The white precipitate, 1,8-bis(4-aza-1-azoniabicyclo[2.2.2]octanyl)octane, was then collected by suction filtration and washed with acetonitrile (3×50 mL) and dried under high vacuum.

Example 2

Synthesis of α,α'-[bis(4-aza-1-azoniabicyclo[2.2.2]octanyl)]p-xylen

A didabco compound containing the ion corresponding to formula (5), i.e., α,α'-[bis(4-aza-1-azoniabicyclo[2.2.2]octanyl)]$_p$-xylene, was prepared as follows: Two equivalents of DABCO (1,4-diazabicyclo[2.2.2]octane) was dissolved in 100 mL of acetonitrile with stirring at room temperature. To the DABCO solution was added one equivalent of α,α'-dibromo-p-xylene while stirring. The resulting reaction mixture was stirred at room temperature for one day, forming a white precipitate. The white precipitate, α,α'-[bis(4-aza-1-azoniabicyclo[2.2.2]octanyl)]p-xylene, was then collected by suction filtration and washed with acetonitrile (3×50 mL) and dried under high vacuum Example 3

General Materials and Methods

The ion channel subunit genes are in expression vectors that facilitate in vitro transcription of channel cRNA using the Ambion mMessage mMachine in vitro transcription kit. cDNA constructs are column-purified, linearized with the appropriate restriction enzyme that cuts a single site following the polyA tail, then purified by precipitation and transcribed in vitro using a promoter, such as T7, T3 and SP6. Transcribed cRNA is purified by precipitation and resuspended in RNAse-free water ready for injection. Each transcription can provide enough cRNA for several months of experiments.

Stage V-VI *Xenopus* oocytes are separated into small groups using forceps, defolliculated by agitation in $Ca^{2+}$-free Ringer solution containing collagenase for one hour, washed, then stored at 15° C. in full Ringers solution before injection. cRNA sufficient to give 1-10 μA of current at physiological voltages for each channel type is injected into *Xenopus* oocytes (selected by appearance for overall health and uniformity of color) using a Sutter manual injector (typically 0.1-5 ng cRNA in a volume of 25-50 nl). The oocytes are then stored for 1-3 days at 15° C. before TEVC recording. Beta subunit cRNA is co-injected as appropriate, typically 2 ng per oocyte.

Whole cell oocyte experiments are performed using a Warner OC-725C amplifier and pClamp9 software with oocytes bathed in a small-volume Warner oocyte bath and viewed with a Fisher dissection microscope. Bath solution for whole cell oocyte recordings, e.g., for potassium channel analysis, is generally (in mM): 96 NaCl, 4 KCl, 1 $MgCl_2$, 0.3 $CaCl_2$, 10 HEPES (Ph 7.4); whole-cell oocyte TEVC pipettes are filled with 3 M KCl. Oocyte patches are studies using an Axon Instruments small-volume bath, viewed with an Olympus IX50 inverted microscope, and recordings made using an Axon Multiclamp 700 A Amplifier and pCLAMP9 software (Axon Instruments). Extracellular solution, e.g., for potassium channel analysis, is generally (in mM): 135 NaCl, 5 KCl, 1.2 $MgCl_2$, 5 HEPES, 2.5 $CaCl_2$, 10 D-glucose (Ph 7.4). Intracellular solution, e.g., for potassium channel analysis, is generally (in mM): 10 NaCl, 117 KCl, 2 $MgCl_2$, 11 HEPES, 11 EGTA, $ICaCl_2$ (Ph 7.2). Patch pipettes are approximately 3-5 MΩ resistance when filled with recording solution.

Quantitative aspects of ion action on ion channels are compared using standard pulse protocols. Pulse times and voltages will vary according to which currents are being studied. I/V and G/V curves are typically fit to a standard Boltzmann function: $1/\{1+\exp[(V_{1/2}-V)/V_s]\}$, where $V_{1/2}$ is the half-maximal voltage of activation and $V_s$ the slope factor, for quantification and comparison. Kinetics of drug effects upon wash-in are generally fit with single or multiple exponential functions and values for $\tau$ and amplitude reported. Drug inhibition constants are calculated after generating a dose response curve by fitting with a logistic dose-response function (see equation (i) below). Typically, 5-20 cells per group are recorded from for heterologous expression experiments. Values are to be stated as mean±SEM with statistical significance set at p<0.05 (unpaired students t-test, ANOVA or the Mann-Whitney Rank Sum Test as appropriate).

Injected oocytes, bathed in bath solution containing 4 mM KCl, unless otherwise stated, are impaled with current and voltage electrodes and clamped at −80 mV holding potential using a Warner OC-725C amplifier. For single-voltage dose-response assessment, currents are recorded for several pulses (each of 1-5 s at a frequency of 0.1 Hz depending upon channel type) in the absence of drug, until equilibrium current level is reached, and then during further pulses with bath application of various concentrations of drug, each until equilibrium current inhibition is observed, with a washout phase in between to eliminate the possibility of channel run-down and other non-drug effects. Ooctyes in which currents do not return to within 10% of pre-drug level after washout are discarded. Drug concentrations are chosen to ensure inhibition values between 0 and 90-100% with at least 3 values within the linear portion of the curve so that the inhibition constant (Ki) can be calculated accurately by fitting with a logistic dose-response function (formula (i)) using the Origin 6.1 graph package.

Kv2.1 mutants were constructed using the QuickChange Multi Site-Directed Mutagenesis Kit (Stratagene, La Jolla, Calif.). Mutant Kv2.1 genes (in the pGA1 oocyte expression vector for oocyte expression) were sequenced in their entirety to confirm appropriate mutations and check for inadvertent mutations, and then subcloned into a wild-type pGA1 backbone. For oocyte expression, Kv3.4 was in pBF1, Kv4.2 was in pRAT. cRNA transcripts were produced from SacII-linearized (Kv2.1), MluI linearized (Kv3.4) and NotI-linearized (Kv4.2) DNA templates using the T3 (Kv2.1), SP6 (Kv3.4) and T7 (Kv4.2) mMessage mMachine kits (Ambion, Austin, Tex.). cRNA was quantified by spectrophotometry and its size integrity verified by gel electophoresis. Defolliculated stage V and VI *Xenopus laevis* oocytes (purchased from Nasco, Grand Island, N.Y.) were injected with 5 ng of cRNA encoding Kv2.1, Kv3.4 or Kv4.2. Chinese Hamster Ovary (CHO) cells were transfected with 0.25 μg Kv2.1 cDNA, 2 μg blank plasmid and 2 μg Green fluorescent Protein in pBOB using Supetfect transfection reagent (Qiagen) 24 hours before whole-cell voltage clamp studies.

Whole-cell two-electrode voltage-clamp (TEVC) recordings were performed on X laevis oocytes expressing cloned Kv2.1, Kv3.4 or Kv4.2 using a Warner OC-725C amplifier and pClamp9 (Axon Instruments, Foster City, Calif.) software. Oocytes were bathed in a small-volume Warner oocyte bath and viewed with a Fisher dissection microscope. Bath solution for whole-cell oocyte recordings was (in mM): 96 NaCl, 4 KCl, 0.7 $MgCl_2$, 1 $CaCl_2$, 10 HEPES (pH 7.4); whole-cell oocyte TEVC pipettes were of 0.2-2 M resistance when filled with 3 M KCl. Experiments were performed 24-48 hours after cRNA injection. For assessment of current-voltage relationships in the absence or presence of dabco derivatives, oocytes were held at −80 mV, stepped for 2 seconds at voltages between −80 mV and +60 mV in 20 mV steps (Kv2.1) or between −80 and +50 mV in 10 mV steps (Kv3.4), then held for 500 ms at −40 mV before returning to the holding potential. For assessment of block during wash-in of dabco derivatives at a single voltage, oocytes were held at −80 mV, and repetitively stepped to 0 mV for 2 s with an interpulse interval of 10 s or 60 s as indicated. A range of concentrations of dabco or dabco derivatives were washed in via the bath solution during repetitive single-voltage pulses (after an initial period of 5 pulses with control solution to ensure current stabilization) until equilibrium block was achieved, to establish dose-responses. Inhibited currents are compared to the current at the end of 5-pulse control period, thus some bar graphs show 'control' current values slightly less than 1, and with an error bar, to show how much currents deviate in the absence of drug. Washout was performed after the highest concentration of blocker was washed in. In cases where washout was achieved, only those recordings in which current returned to within 10% of original current level were used for construction of dose-response curves. For cysteine protection experiments using the K356C variant of Kv2.1, a dabco derivative (JC638.2a) was washed in to equilibrium block, followed by wash-in of a solution containing both JC638.2a and MTSET until no further changes in current were seen; following this the solution was washed out with standard bath solution. As controls for this protection analysis, JC638.2a or MTSET were washed in alone until equilibrium block, then washed out.

For whole-cell voltage clamp studies of CHO cells, bath solution was (in mM): 135 NaCl, 5 KCl, 1.2 $MgCl_2$, 5 HEPES, 2.5 $CaCl_2$, and 10 D-glucose, pH 7.4. Pipettes were 3-5 MQ resistance when filled with intracellular solution containing (in mM): 10 NaCl, 117 KCl, 2 $MgCl_2$, 11 HEPES, 11 EGTA, and 1 $CaCl_2$, pH 7.2. For experiments with extracellular drug application, cells were held at −80 mV and subjected to 2 sec test pulses from to 0 mV every 30 s. Whole-cell patch clamp recordings were performed at 22-25° C. using an IX50 inverted microscope equipped with epifluorescence optics for GFP detection (Olympus), a Multiclamp 700 A Amplifier, a Digidata 1300 Analogue/Digital converter and pClamp9 software (Axon Instruments). Leak and liquid junction potentials (<4 mV) were not compensated for when generating current-voltage relationships. For intracellular drug application, the tip of the recording electrode was first filled with drug-free intracellular solution, the electrode was then back-filled with intracellular solution containing TEA (20 mM), TA279 (5 mM) or JC638.2α (0.5 mM). Cells were held at −80 mV and subjected to 2 sec test pulses from −60 mV to +60 mV in 10 mV increments, followed by a 1 sec tail pulse to −30 mV. After an initial recording which we denoted time 0, a second recording was performed after 5 minutes.

Data analysis: Current-voltage relationships were obtained by measuring peak current during depolarizing pulses. Inhibition constants for DABCO blockers were calculated after generating a dose response curve by fitting with a logistic dose-response function $y=A_2+[A_1-A_2/1+(x/x_0)^p]$, where $A_1$ is the maximum response plateau, $A_2$ is the minimum response plateau, x is drug concentrator, $x_0$ is the $IC_{50}$, and p the Hill slope. Data analysis was performed using CLAMPFIT 9 (Axon Instruments, Foster City, Calif.) and tabulated in Excel 5.0. Graphs were generated using Origin 6.1. Data are expressed as mean±SEM, with n specifying the number of independent experiments. Statistical significance was assessed by one-way ANOVA with p<0.05 being indicative of significance.

Example 4

Kv2.1 Channels are Inhibited by Two Monocationic Compounds

We explored blocking effects on Kv2.1 with and without the MiRP2 ancillary subunit. Kv2.1 can co-assemble with MiRP2 in rat brain. The sensitivities of two diammonium compounds (JE188 and TA279) were analyzed by functional expression in Xenopus oocytes using two-electrode voltage clamp (TEVC), and bath application of the compounds at various concentrations. Dose-response curves were fitter with a logistic dose-response function:

$$y = A_2 = (A_1/1 = (x/x_0)^p)$$ Equation (i)

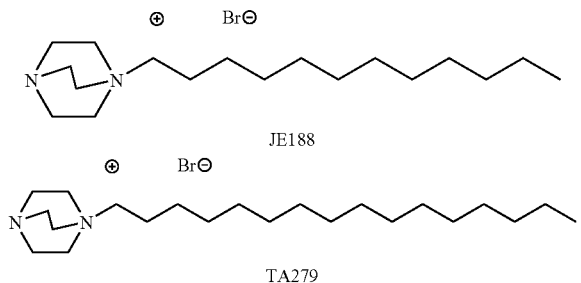

JE188

TA279

Figure 1B:
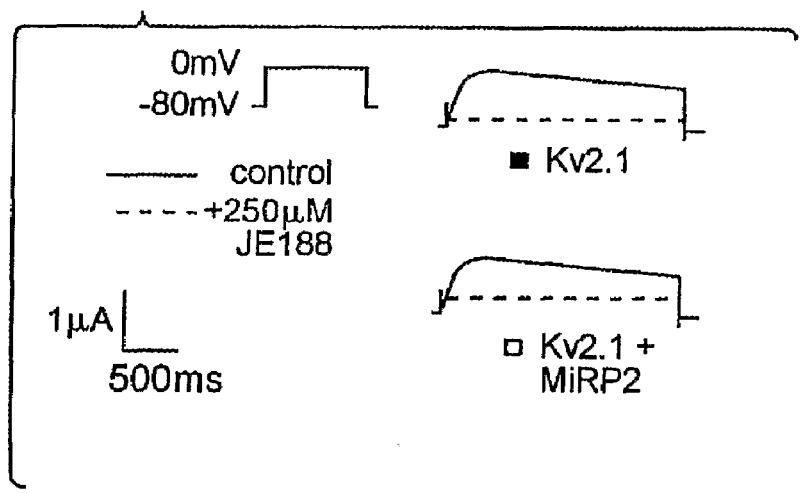
Figure 1C:
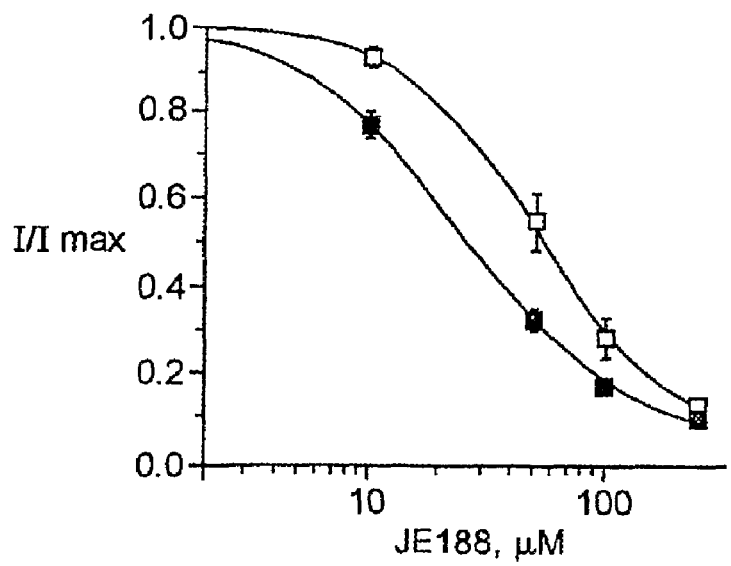

JE 188 compound, when applied externally to whole oocytes via the bath, inhibited Kv2.1 currents with or without MiRP2 (see FIG. 1). MiRP2 caused a two-fold decrease in sensitivity (Kv2.1: $x_0$=23.3±2.1 μM, p=1.4±0.1; MiRP2-Kv2.1: $x_0$=49.2±8.2 μM, p=1.6±0.2). This shift is in contrast to the two-fold increase in tetraethylammonium affinity observed for MiRP2-KV2.1 channels compared to Kv2.1 alone. Importantly, Kv2.1 currents are 500-fold more sensitive to block by JE188 than to block by tetraethylammonium.

Figure 2A:
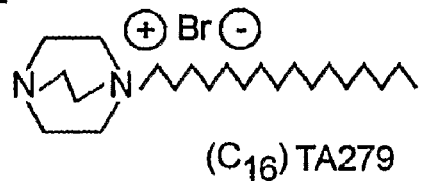
FIG. 2. TA279 is a potent blocker of Kv2.1 channels. (A) The structure of compound TA 279. (B) Representative traces of currents recorded in *Xenopus* oocytes using two-electrode voltage clamp, and voltage protocol in upper left. Oocytes were injected with cRNA encoding Kv2.1+/−cRNA encoding MiRP2, as indicated. Scale as indicated in lower left. 'Control' trace (solid line) was recorded after 5 pulses in normal 4 mM KCl bath medium (pH 7.4). Dashed line indicates equilibrium trace during pulsing in the presence of 5 μM TA279. (C) Mean current inhibition assessed by comparison of peak current at various drug concentrations with peak current before drug application (n=4-6 oocytes per point; error bars indicate SEM). Drug block was reversible upon washout and traces that did not recover to control peak current (+/−10%) upon washout were discarded.
Figure 2B:
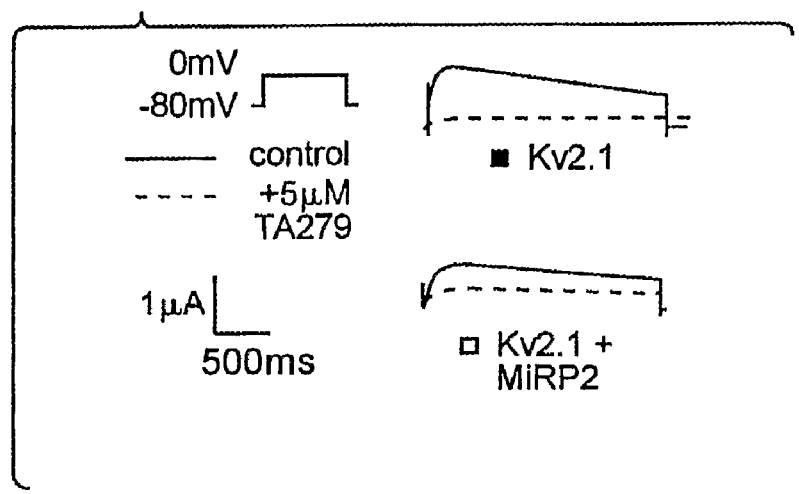
Figure 2C:
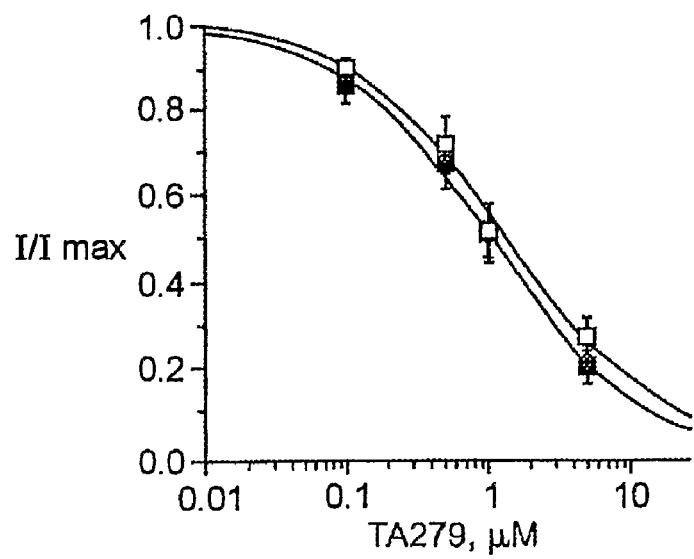

TA279 was also applied externally to whole oocytes expressing Kv2.1 with or without MiRPs, via the bath medium (FIG. 2). TA279 has a longer carbon string (C16 versus C12). Application of various doses of TA279 and fitting of the dose response curve for current inhibition showed that MiRP2 did not significantly alter inhibition of Kv2.1 channels by TA279 (Kv2.1: $x_0$=1.0±0.8 μM, p=0.8±0.1 MiRP2-Kv2.1: $x_0$=1.3±0.4 μM, p=0.8±0.2). Significantly, Kv2.1 currents are 10,000-fold more sensitive to TA279 than to tetraethylammonium, and 20-fold more sensitive to TA279 than to JE188.

Example 5

Didabco Strings are a Class of Kv Channel-Reactive Agents

Figure 3A:
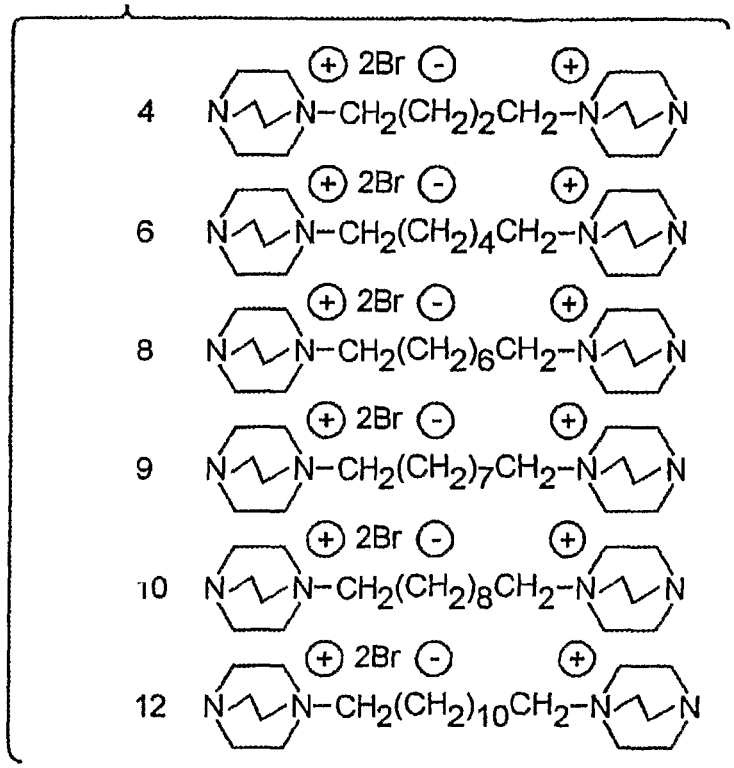
FIG. 3. Didabco strings differentiate between different channels, and can block or open. (A) Structures of six didabco strings, differing only in the number of $CH_2$ groups in the string (4-12). (B) Effects of each of the six didabco strings (at 1 mM, externally applied via the bath) on peak $K^+$ currents recorded at 0 mV during 0.1 Hz, 2 s pulses from −80 mV using TEVC in whole oocytes injected with cRNA for Kv2.1, Kv3.4 or KCNQ4. A Kv3.4 variant lacking the inactivation ball domain (deletion 1-28) was used in this study. Values shown are compared to pre-drug level (=1) and are the mean of the peak current recorded at equilibrium from 2-6 experiments. Error bars indicate SEM. Thus values <1 indicate channel "block," values >1 indicate channel 'opening' by the compound.
Figure 3B:
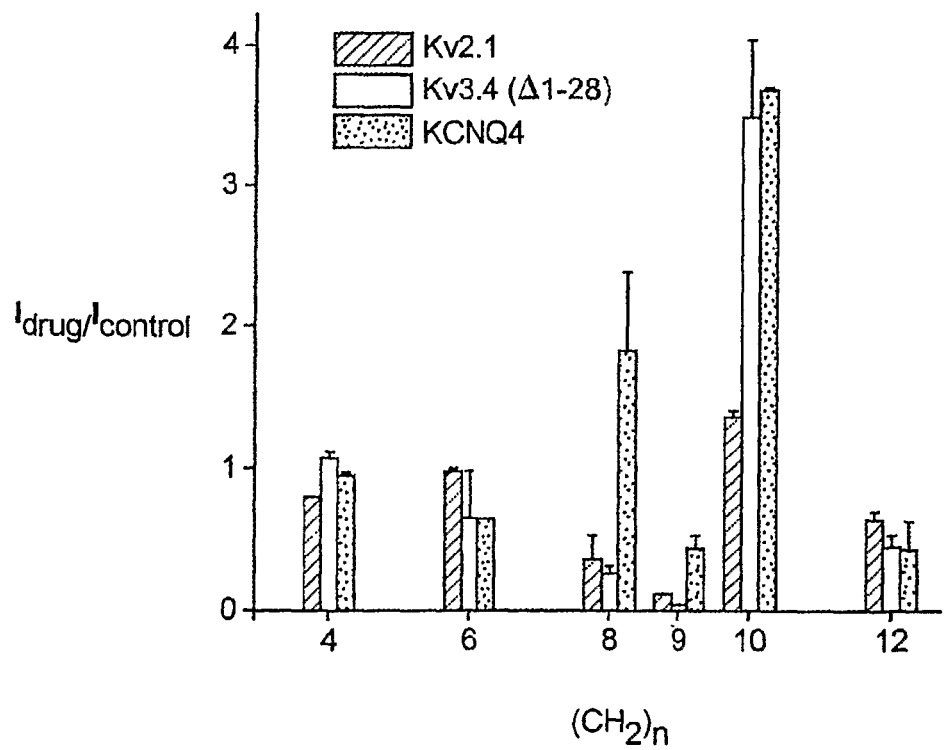

We performed a screen to examine the effects of didabco strings (e.g., compounds with a dabco group at either end, differing from one another in the number of $CH_2$ groups separating the two dabco groups) (see FIG. 3). Structure I below represents a dabco group.

Structure I

Three representative Kv channels were tested: 1) Kv2.1 (a low tetraethylammonium-affinity delayed rectifier highly expressed in mammalian brain and heart), 2) Kv3.4 (a high-tetraethylammonium-affinity A-type channel for controlling skeletal muscle excitability and neuronal refractoriness) and 3) KCNQ4 (a mid-range tetraethylammonium-affinity channel associated with inherited deafness and involved in diseases involving neuronal hyperexcitability).

The data demonstrate that various didabco strings possess several notable properties. These properties include: (i) differentiation between the three channel types; (ii) varied effects depending on chain length; and (iii) a capacity to 'open', i.e. increase Kv current in some cases, while blocking in others.

Figure 4A:
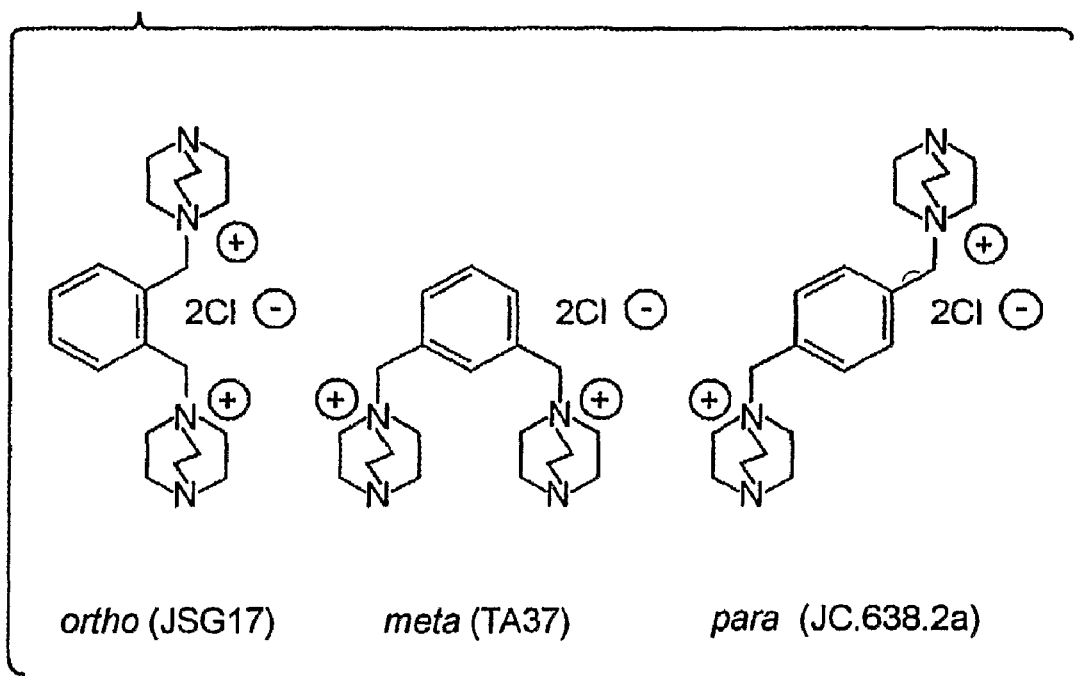
FIG. 4. Aromatic ring-separated didabco stings differentiate between different channels. (A) Structures of three didabco strings, differing only in the positioning of the dabco groups around an aromatic ring. (B) Effects of each of the three didabco strings (at 1 mM, externally applied) on peak K$^+$ currents recorded at 0 mV using TEVC in *Xenopus* oocytes expressing Kv2.1, Kv3.4 lacking 1-28, or KCNQ4. Values shown are compared to pre-drug level (=1) and are the mean value from 2-8 experiments. Error bars indicate SEM.
Figure 4B:
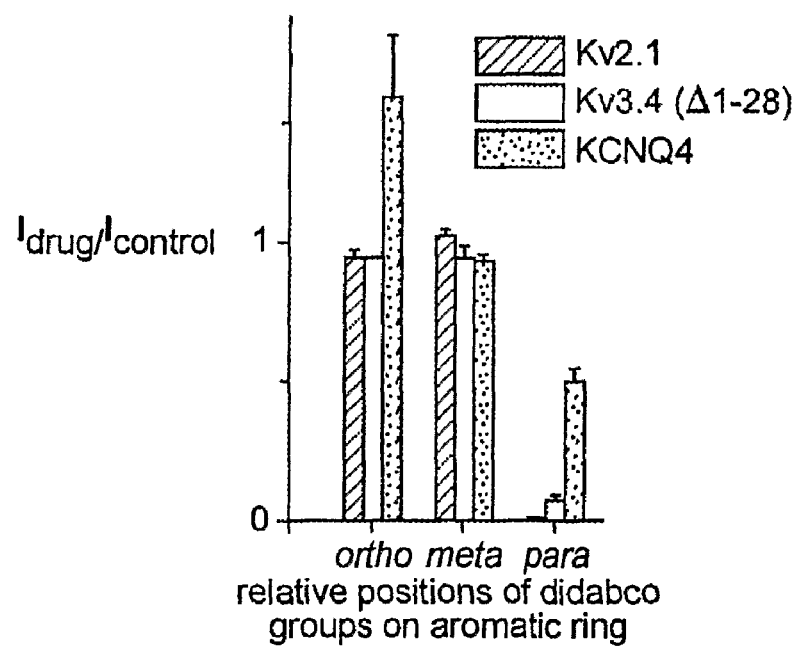

In a further experiment, we tested the same three Kv channels for sensitivity to members of another class of didabco compounds. The didabco groups in these compounds are separated by an aromatic ring, and they differ only in the relative positioning of the dabco groups on that ring (ortho, meta, para) (FIG. 4A). The compounds each behave distinctly from one another and show channel-type dependence of block. One compound (ortho JSG 17) is a KCNQ4-specific opener (1 mM, within the group of three channels tested, FIG. 4B).

Example 6

The TG28 Didabco String and Kv2.1

Figure 5:
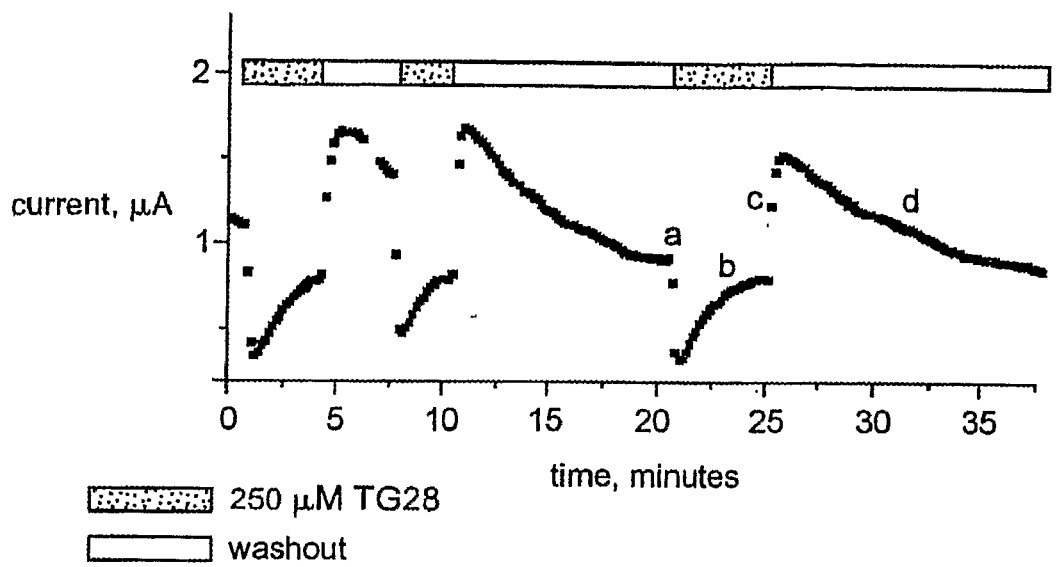
FIG. 5. TG28 (the didabco string with 12 CH$_2$ groups shown in FIG. 3) blocks and partially recovers Kv2.1 wash-in, opens Kv2.1 during wash-out. Peak currents (filled squares) recorded at 0 mV during successive 0.1 Hz, 2 s pulses from −80 to 0 mV recorded in *Xenopus* oocytes using two-electrode voltage clamp, and voltage protocol in upper left, during three cycles of wash-in (upper solid line) and washout (upper open line) of 250 μM TG28 in 4 mM KCl bath medium (pH 7.4). Oocytes were injected with cRNA encoding Kv2.1. Four phases are highlighted with letters a-d on the final cycle of the three: a. rapid block during wash-in, b. slow partial recovery of current during wash-in, c. rapid recovery and overshoot during wash-out, and d. slow relaxation to original (pre-drug) current during wash-out.

TG28 is a didabco string with 12 $CH_2$ groups separating the two dabco groups, which was shown in FIG. 3 to block Kv2.1. Further review of this block revealed a striking effect: rapid reduction of current (block) followed by slow, partial restoration of current (partial opening). Subsequent 'washout' of TG28 resulted in a rapid increase of Kv2.1 current to a level, on average, two-fold larger than the pre-drug current, then a slow decrease to pre-drug current levels (FIG. 5).

Based on the data, TG28 is a Kv2.1 blocker from the outside, but a Kv2.1 opener from the inside. Alternatively, there are two different external TG28 binding sites on Kv2.1 with different binding affinities and functional consequences.

Example 7

Didabco Compounds Act Within the Kv Channel Permeation Pathway

To investigate the mechanism of Kv channel block or opening by didabco compounds, the current-voltage relationship (I/V curve) of Δ1-28 Kv3.4 channels expressed in Xenopus oocytes was assessed using TEVC recording in the absence and presence of a didabco opener (JC279.3a, the 10 $CH_2$-group didabco from FIG. 3) or a didabco blocker (JC638.2a, the para didabco from FIG. 4).

Figure 6:
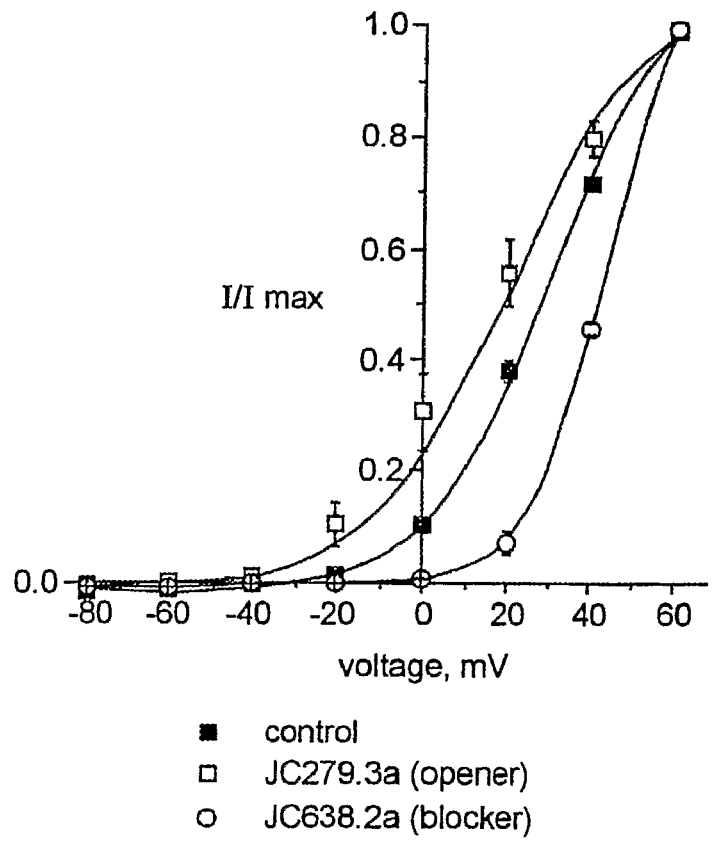
FIG. 6. Opening and block of Kv3.4 by two didabco compounds show voltage-dependency. JC279.3a is the didabco string with 10 CH$_2$ groups shown in FIG. 3. JC638.2a is the para didabco string shown in FIG. 4. Normalized I/V relationship for Δ1-28 Kv3.4 currents in oocytes in the absence (control) or presence as indicated of 1 mM JC279.3a or JC638.2a. Peak currents during 2 s pulses to voltages between −80 and +60 mV (protocol upper left insert) were recorded, before and after drug was washed in during successive 0.1 Hz, 2 s pulses from −80 to 0 mV until equilibrium block or opening was observed. Points are means from n=3-16 oocytes; error bars indicate SEM.

FIG. 6 shows that block or opening of Kv3.4 by JC279.3a or JC638.2a is voltage-dependent. Specifically, block or opening of Kv3.4 channels by these two didabco compounds was attenuated at more depolarized (positive) voltages.

Example 8

Kv2.1 and Kv3.4 Channels are Differentially Inhibited by DABCO Monostrings

Blocking effects of non-substituted DABCO on Kv2.1 and Kv3.4 potassium channels were examined. Kv2.1 is a delayed rectifier Kv channel expressed in mammalian heart, brain and other excitable tissues. In particular, Kv2.1 facilitates dynamic control of neuronal excitability, forms a component of the IK cardiac myocyte repolarization current in rodent heart, and generates an O2-sensitive current in pulmonary arteries. Kv3.4 is a fast-inactivating Kv channel expressed primarily in the brain and skeletal muscle. Co-assembly of Kv3.4 with delayed rectifier Kv3 subfamily a subunits in the brain is thought to generate heteromeric channels with differing inactivation rates, perhaps enhancing firing rate of fast-spiking neurons. In skeletal muscle, Kv3.4 forms complexes with the MiRP2 ancillary subunit to control myocyte excitability and repolarization.

Bath-applied DABCO, at 1 mM had no effects on the magnitude or kinetics of either Kv2.1 or Kv3.4 currents heterologously expressed in *X. laevis* oocytes, analyzed by two-electrode voltage clamp (TEVC). Next, the sensitivities of Kv2.1 and Kv3.4 to two DABCO-derived monostrings, JE188 and TA279, were analyzed by functional expression in *X. laevis* oocytes using TEVC and bath application of the compounds at various concentrations.

The JE188 12-carbon monostring DABCO compound significantly inhibited both Kv2.1 and Kv3.4 channels at 50 µM, with 250 µM producing almost complete inhibition in both cases. Fitting of dose response curves with a logistic dose response function yielded JE188 an inhibition constants $IC_{50}$ of 23.3±2.1 µM, slope=1.4±0.1 for Kv2.1; and an $IC_{50}$ of 34.2±10 µM, slope=0.7±0.1 for Kv3.4.

Recording of current-voltage 'families' for both channel types in the presence and absence of JE 188 showed voltage dependence of block in both cases such that inhibition was much less pronounced at more positive voltages. For Kv2.1 channels, mean inhibition was 3-fold more at 0 mV than at +60 mV; for Kv3.4 channels mean inhibition was 2-fold more at 0 mV than at +50 mV. For Kv3.4 channels, crossover of the N-type inactivation occurred with application of 50 µM JE188, suggesting either slowing of inactivation or partial drug unbinding at depolarized voltages.

The TA279 16-carbon monostring DABCO compound is a potent compound, inhibiting both Kv2.1 and Kv3.4 channels at 1 µM, with 5 mM producing almost complete inhibition in both cases. Fitting of dose response curves with a logistic dose response function yielded an $IC_{50}$ of 1.9±3.6 µM, slope=0.6±0.4 for Kv2.1; and an $IC_{50}$ of 0.6±0.1 µM, slope=2.8±1.1 for Kv3.4. These values indicate that Kv2.1 channels are 3,000-fold more sensitive to block by externally-applied TA279 than to block by externally-applied TEA, and Kv3.4 channels are 500-fold more sensitive. Block of Kv2.1 and Kv3.4 was again voltage-dependent; mean inhibition of Kv2.1 channels was 3-fold more at 0 mV than at +60 mV; for Kv3.4 channels mean inhibition was 1.5-fold more at 0 mV than at +50 mV. For Kv3.4 channels, N-type inactivation was relatively less complete (as a proportion of peak current) in the presence of TA279.

It was considered possible that unlike TEA, externally-applied TA279 might cross the plasma membrane to access a higher-affinity internal site. TEA has a higher-affinity site in the inner pore of Kv channels, but can only access it when applied internally. Indeed, TA279 washout was much slower than typically observed for TEA, taking several minutes, suggesting the possibility of it crossing the plasma membrane to exert its action.

To assess at which side this DABCO derivative acts, TA279 was applied extracellularly (via the bath) and intracellularly (via the recording electrode) to Kv2.1 channels expressed in CHO cells. Extracellular application of 500 nM TA279 produced a mean current inhibition of 59±4% at 0 mV (n=3), indicating ~4-fold higher sensitivity than Kv2.1 channels expressed in oocytes, a common phenomenon because oocytes are thought to sequester some drugs, decreasing apparent sensitivity. Intracellular application of a ten-fold higher concentration of TA279 (5 µM) produced no significant block at 0 mV, either at 0 or 5 minutes after attaining the whole-cell configuration, compared to control currents in which no drug was added to the electrode, as assessed by one-way ANOVA (n=4). As a positive control, 20 mM tetra-ethylammonium (TEA) was shown to produce ~85% block at 0 mV at time 0 and ~88% block after 5 minutes. These data demonstrates that the high affinity site of TA279 is accessed from outside the cell and does not require TA279 to cross the plasma membrane.

Simple diDABCO strings, with a DABCO group at each end separated by a variable-length hydrocarbon chain, also inhibited both Kv2.1 and Kv3.4 channels but with lower affinity to the two monostrings tested. TG26 (4-carbon string) was less effective than TG27 (8-carbon string) at inhibiting either channel at a concentration of 1 mM and in the case of both compounds Kv2.1 was more sensitive than Kv3.4.

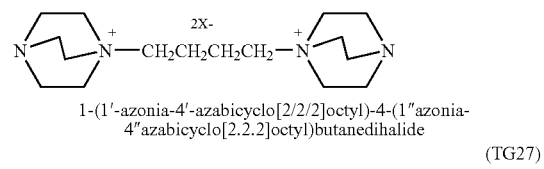

1-(1'-azonia-4'-azabicyclo[2/2/2]octyl)-4-(1″azonia-4″azabicyclo[2.2.2]octyl)butanedihalide (TG26)

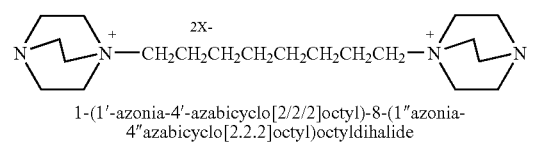

1-(1'-azonia-4'-azabicyclo[2/2/2]octyl)-8-(1″azonia-4″azabicyclo[2.2.2]octyl)octyldihalide (TG27)

Construction of dose response curves yielded an $IC_{50}$ for TG27 of 270.5±66.4 µM, slope=2.1±0.8 for Kv2.1; Kv3.4 appeared somewhat less sensitive but an accurate fit of the dose response curve could not be achieved because application of TG27 at concentrations above 1 mM began to introduce nonspecific leak. Similarly, construction of dose responses for TG26 was not possible because doses required to produce >50% block were toxic to the oocytes.

Even greater differentiation between the potency of similar compounds for a given channel was observed with diDABCO compounds separated by an aromatic group. Three such compounds of similar structure except for the relative positioning of the DABCO groups on the aromatic were assessed: JSG17, TA37 and JC638.2α, which contain DABCO groups in ortho, meta and para positions, respectively, around the central aromatic ring (FIG. 4A). For both Kv2.1 and Kv3.4, only the para compound, JC638.2α, showed significant inhibition at 1 mM, indicating the critical nature of the shape of the compound in determining block. JC638.2α did not, however, significantly differentiate between Kv2.1 and Kv3.4 in terms of sensitivity. Dose response curves yielded an $IC_{50}$ for JC638.2α of 185.7±17 µM, slope=1.4±0.1 for Kv2.1; and an $IC_{50}$ of 129±20.7 µM, slope=1.3±0.2 for Kv3.4. As with the DABCO monostrings, JC638.2α showed voltage dependent block, with inhibition being attenuated at more positive voltages.

The sensitivity of Kv4.2, a fast-inactivating Kv channel with relatively low sensitivity to TEA compared to Kv2.1 and Kv3.4, was also screened for sensitivity to representative DABCO derivatives. Kv4.2 generates A-type currents in mammalian brain and generates the cardiac $I_{to}$ current in some species. As with previous reports for TEA, Kv4.2 was relatively insensitive to DABCO derivatives, showing 3% block with 100 µM JE188, 3% block with 1 mM TG27, and 38% block with 0.5 mM JC638.2α. Thus, DABCO compounds, in particular simple monostrings and diDABCO strings, can be used to differentiate between transient outward currents generated by Kv3.4 versus Kv4.2, and at much lower concentrations than, for example, TEA. This property may prove useful in distinguishing between different A-type currents in the brain in regions where both Kv3.4 and Kv4.2 are expressed, such as the hippocampus.

Example 9

JC638.2a Binds at a Similar External Site to TEA in Kv2.1

Generation of V curves from current-voltage families recorded in the presence or absence of DABCO derived compounds such as JC638.2a indicated voltage dependence of block. This may suggest that DABCO derivatives block within the ion conduction pathway, as observed for TEA. To explore this hypothesis further block of wild-type and mutant Kv2.1 channels by JC638.2α was analyzed. First, JC638.2α was applied intracellularly to Kv2.1 channels expressed in CHO cells, via the recording electrode. As with TA279, intracellularly applied JC638.2α (0.5 mM) produced no significant block at 0 mV when compared to control recordings with no drug in the recording electrode, as assessed by one-way ANOVA (n=4-5) whereas inparallel positive control experiments intracellularly applied TEA (20 mM) produced 70% and 80% block at 0 mV at 0 and 5 minutes respectively (n=3-5). This suggested that JC638.2α-blocked via an external, not internal, site.

Effects of the Y380T mutation in Kv2.1 on block by JC.638.2α was compared. It was found that the mutation did not alter block by JC638.2α, giving an $IC_{50}$ of 185±41 µM, slope=1.3, not significantly different from wild-type.

Methanethiosulfonate (MTS) forms the basis for a group of compounds that are able to bind irreversibly to the free sulfhydryl group of cysteine residues that line the pore of channels. Introduction of a cysteine at position 356 in Kv2.1 made this position modifiable with MTSET resulting in permanent fractional block. However, when TEA was administered before MFSET this ability to permanently modify the introduced cysteine was lost. Thus, TEA protects Kv2.1 channels from MTSET modification, suggesting an external TEA binding site further from the pore than Kv2.1 residue K356, more distal from the pore than Y380. The ability of JC638.2α to prevent modification by MTSET at Kv2.1-K356C, because of similarities between the effects of some DABCO compounds and TEA, was investigated. When JC638.2α was administered alone, the K356C mutant was inhibited by 62±3%; this block was reversed with washout. When MTSET was used to modify the introduced cysteine, currents were inhibited 56±3%; washout here was incomplete, leaving 244% current inhibition remaining. Pre-application of JC638.2α prevented permanent modification of Kv2.1-K356C: co-application of JC638.2 (and MTSET inhibited K356C-Kv2.1 current by 84±1%, completely reversible with washout. These effects are similar to those previously observed for protection from MTSET modification of Kv2.1-K356C by TEA, and together with the lack of effect of intracellularly applied JC638.2α, suggest that JC638.2α binds to a similar external site in Kv2.1 to TEA.

What is claimed is:

1. A method for modulating a potassium ion channel in a mammal in need thereof, the method comprising administering to the mammal an effective amount of an ion wherein the ion is represented by:

$$\text{(3a)}$$

wherein X represents a straight-chained or branched hydrocarbon group having one to twenty six carbons atoms.

2. A method according to claim 1, wherein X represents a straight-chained or branched hydrocarbon group having four to twelve carbon atoms.

3. A method according to claim 2, wherein X represents —$(CH_2)_8$—.

4. A method according to claim 2, wherein X represents —$(CH_2)_9$—.

5. A method according to claim 2, wherein X represents —$(CH_2)_{10}$—.

6. A method according to claim 2, wherein X represents —$(CH_2)_{12}$—.

7. A method according to claim 1, wherein the potassium ion channel is voltage gated.

8. A method according to claim 1, wherein the potassium ion channel is ATP gated.

9. A method according to claim 1, wherein the potassium ion channel is calcium activated.

10. A method according to claim 1, wherein the potassium ion channel is an inward rectifier.

11. A method according to claim 1, wherein the potassium ion channel is any one of the potassium ion channels shown in Table 1 and Table 2.

12. A method according to claim 1, wherein modulating a potassium ion channel is opening a potassium ion channel.

13. A method for opening a potassium ion channel in a mammal in need thereof, the method comprising administering to the mammal an effective amount of an ion wherein the ion is represented by:

$$\text{(3a)}$$

wherein X represents a straight-chained or branched hydrocarbon group having one to twenty six carbons atoms.

14. A method according to claim 13, wherein X represents a straight-chained or branched hydrocarbon group having four to twelve carbon atoms.

15. A method according to claim 13, wherein X represents —$(CH_2)_{10}$—.

16. A method according to claim 13, wherein the potassium ion channel is voltage gated.

17. A method according to claim 13, wherein the potassium ion channel is ATP gated.

18. A method according to claim 13, wherein the potassium ion channel is calcium activated.

19. A method according to claim 13, wherein the potassium ion channel is an inward rectifier.

20. A method according to claim 13, wherein the potassium ion channel is any one of the potassium ion channels shown in Table 1 and Table 2.

* * * * *